US00RE41287E

(19) United States
(12) Reissued Patent
Fairlie et al.

(10) Patent Number: US RE41,287 E
(45) Date of Reissued Patent: Apr. 27, 2010

(54) CYCLIC AGONISTS AND ANTAGONISTS OF C5A RECEPTORS AND G PROTEIN-COUPLED RECEPTORS

(75) Inventors: David Fairlie, Springwood (AU); Stephen Maxwell Taylor, Bellbird Park (AU); Angela Monique Finch, Narangba (AU); Allan Wong, Bundaberg (AU)

(73) Assignee: Promics Pty Limited, New South Wales (AU)

(21) Appl. No.: 12/045,088

(22) PCT Filed: Jun. 25, 1998

(86) PCT No.: PCT/AU98/00490

§ 371 (c)(1), (2), (4) Date: Apr. 21, 2000

(87) PCT Pub. No.: WO99/00406

PCT Pub. Date: Jan. 7, 1999

Related U.S. Patent Documents

Reissue of:
(64) Patent No.: 6,821,950
Issued: Nov. 23, 2004
Appl. No.: 09/446,109
Filed: Apr. 21, 2000

(30) Foreign Application Priority Data

Jun. 25, 1997 (AU) ..... PO7550

(51) Int. Cl.
*A61K 38/00* (2006.01)
*A61K 38/12* (2006.01)
*C07K 17/00* (2006.01)

(52) U.S. Cl. ..... 514/9; 514/12; 514/13; 514/14; 514/15; 514/16; 514/17; 530/317; 530/323; 530/324; 530/325; 530/326; 530/327; 530/328; 530/329

(58) Field of Classification Search ..... 514/9, 514/12, 13, 14, 15, 16, 17; 530/317, 323, 530/324, 325, 326, 327, 328, 329
See application file for complete search history.

(56) References Cited

U.S. PATENT DOCUMENTS

| | | | |
|---|---|---|---|
| 5,386,011 | A | 1/1995 | Wiedeman et al. |
| 5,696,230 | A | 12/1997 | Sanderson et al. |
| 5,807,824 | A | 9/1998 | van Ostrum et al. |
| 6,821,950 | B1 | 11/2004 | Fairlie et al. |
| 2006/0160726 | A1 | 7/2006 | Fairlie et al. |
| 2006/0217530 | A1 | 9/2006 | Maxwell et al. |

FOREIGN PATENT DOCUMENTS

| | | |
|---|---|---|
| WO | 92/11858 | 7/1992 |
| WO | 95/16033 | 6/1995 |
| WO | 95/25957 | 9/1995 |

OTHER PUBLICATIONS

G. Abbenante, et al., "Regioselective Structural and Functional Mimicry of Peptides. Design of Hydrolytically–Stable Cyclic Peptidomimetic Inhibbitors of HIV–1 Protease", J. Am. Chem. Soc. (1995), 117, 10220–10226.
David K. Chalmers, et al., "Pro–D–NMe–Amino Acid and D–Pro–NMe–Amino Acid: Simple, Efficient Reverse–Turn Constraints", J. Am. Chem. Soc. (1995), 117, 5927–5937.
W.L. Duax, et al., "Molecular Structure and Mechanisms of Action of Cyclic and Linear Ion Transport Antibiotics", Biopolymers (1996), vol. 40: 141–155.
Otto D. Hensens, et al., The Journal of Antibiotics, (1991), vol. 44, No. 2, 249–254.
Julie A. DeMartino, et al., "Arginine 206 of the C5a Receptor Is Critical for Ligand Recognition and Receptor Activation by C–terminal Hexapeptide Analogs", The Journal of Biological Chemistry vol. 370, No. 27, Jul. 1995, 15966–15969.
Julie A. DeMartino, et al., "The Amino Terminus of the Human C5a Receptor Is Required for High Affinity C5a Binding and for Receptor Activation by C5a but Not C5a Analogs", The Journal of Biological Chemistry, vol. 269, No. 20, pp. 14446–14450, 1994.
Julia A. Ember, et al., "Biologic Activity of Synthetic Analogues of C5a Anaphylatoxin", The Journal of Immunology, vol. 148, No. 10, 3165–3173 , 1992.
Zenon D. Konteatis, et al., "Development of C5a Receptor Antagonists Differential Loss of Functional Responses" J. Immunol., (1994), 153: 4200–4205.
S.M. Vogen, et al., Journal of Peptide Research, vol. 51, pp. 226–234, "NMR Analysis of a Potent Decapeptide Agonist of Human C5a Anaphylatoxin", Mar. 1998.
R.M. Tempero, et al., Journal of Immunology, vol. 158, No. 3, pp. 1377–1382, "Molecular AdJuvant Effects of A Conformationally Biased Agonist of Human c5a Anaphylatoxin", Feb. 1997.
L. Baranyl, et al., Journal of Immunology, vol. 157, No. 10, pp. 4591–4601, "Antisense Homology Boxes In C5a Receptor And C5a Anaphylatoxin", Nov. 1996.
R. Kawatsu, et al., Journal of Pharmacology and Experimental Therapeutics, vol. 278, No. 1, pp. 432–440, "Conformationally Biased Analogs of Human C5a Mediate Changes in Vascular Permeability", (1996).
Y. Kaneko, et al., Immunology, vol. 86, pp. 149–1554, "Antagonist Peptides Against Human Anaphylatoxin C5a", (1995).
M. Kawai, et al., Journal of Medicinal Chemistry, vol. 34, No. 7, pp. 2068–2071, "Identification and Synthesis of a Receptor Binding Site Of Human Anaphylatoxin C5a",Jul. 1991..

(Continued)

*Primary Examiner*—Cecilia Tsang
*Assistant Examiner*—Abdel A Mohamed
(74) *Attorney, Agent, or Firm*—Oblon, Spivak, McClelland, Maier & Neustadt, L.L.P.

(57) ABSTRACT

The present invention relates to novel cyclic or constrained acyclic compounds which modulate the activity of G protein-coupled receptors and are useful in the treatment of conditions mediated by G protein-coupled receptors, for example, inflammatory conditions.

54 Claims, 11 Drawing Sheets

OTHER PUBLICATIONS

Z.D. Koneatis, et al., Journal of Immunology, vol. 153, No. 9, pp. 4201–4205, "Development of C5a Receptor Antagonists", Nov. 1994.
S.D. Sanderdon, et al., Journal of Medicinal Chemistry, vol. 38, No. 18, pp. 3669–3675, "Decapeptide Agonists of Human C5a: The Relationship Between Conformation and Neutrophil Response" Sep. 1995.
A.M. Finch, et al., Journal of Medicinal Chemistry, vol. 40, No. 6, pp. 877–884, "Biologically Active Conformer of the Effector Region of Human C5a and Modulatory Effects of N–Terminal Receptor Binding Determinants on Activity", Mar. 1997.
M. Kawai, et al., Journal of Medicinal Chemistry, vol. 35, No. 2, pp. 220–223, "Structur–Function Studies in a Series of Carboxyl–Terminal Octapeptide Analogues of Anaphylatoxin C5a" Jan. 1992.
G. Drapeau, et al., Biochemical Pharmacology, vol. 45, No. 6, pp. 1289–1299, "Synthetic C5a Receptor Agonists", Mar. 1993.
J.A. DeMartino, et al., Journal of Biological Chemistry, vol. 27, No. 27, pp. 15966–15969, "Arginine 206 of the C5a Receptor is Critical for Ligand Recognition and Receptor Activation by C–Terminal Hexapeptide Analogs", Jul. 1995.
X–Zhang, et al., Protein Science, vol. 6, pp. 65–72, "Solution Structure of Unique C5a Semi–Synthetic Antigonist: Implications in Receptor Binding", Jan. 1997.
T.C. Pellas, et al., Journal of Immunology, vol. 160, pp. 5616–5621, "Novel C5a Receptor Antagonists Regulate Neutrophol Functions in vitro and in vivo", Jun. 1998.
Paczkowski, et al., British Journal of Pharmacology, "Pharmacological Characterization of Antagonists of the C5a Receptor", vol. 128, No. 7, pp. 1461–1466, 1999.
A.K. Wong, et al., Journal of Medicinal Chemistry, vol. 41, No. 18, XP–002200381, pp. 3417–3425, "Small Molecular Probes for G–Protein–Coupled C5a Receptors: Conformationally Constrained Antagonists Derived From the C Terminus of the Human Plasma Protein C5a", Aug. 27, 1998.
Siciliano et al, Two–Site Binding of C5a by its Receptor. An Alternative Binding Paradigm for G Protein–Coupled Receptors (1994) Proc. Nat. Sci. USA, 91 (4), pp. 1214–1218.
U.S. Appl. No. 12/045,088, filed Mar. 10, 2008, Fairlie, et al.
Ryohei F, Tsuji, et al., "Anti–inflammatory effects and specificity of L–156, 602: comparison of effects on concanavalin A and zymosan–induced footpad edema, and contact sensitivity response", Immunopharmacology, 29 (1995) 79–87.
Sam D. Sanderson, et al., "Decapeptide Agonists of Human C5a: The Relationship between Conformation and Spasmogenic and Platelet Aggregatory Activities", J. Med. Chem. (1994), 37, 31771–3180.
Sam D. Sanderson, et al., "Decapeptide Agonists of Human C5a: The Relationship between Conformation and Neutrophil Response", J. Med. Chem., (1995), 38 3669–3675.
Allan K. Wong, et al., "Small Molecular Probes for G–Protein–Coupled C5a Receptors: Conformationally Constrained Antagonists Derived from the C terminus of the Human Plasma Protein C5a" J. Med. Chem. (1998), 41, 3417–3425.
Salvatore J. Siciliano, et al., "Two–site binding of C5a by its receptor: An alternative binding paradigm for G protein–coupled receiptors", Proc. Natl. Acad. Sci., vol. 91, pp. 1214–1218, (Feb. 1994).
Sam D. Sanderson, et al., "Decapeptide Agonists of Human C5a: The Relationship between Conformation and Neutrophil Response", J. Med. Chem. (1995), 38, 3669–3675.
Ryohei F. Tsuji, et al., "Preferential suppression of Delay–type Hypersensitivity by L–156,602, a C5a Receptor Antagonist", Biosci. Biotech. Biochem,. 56, (10), 1686–1689, 1992.
Ryohei F. Tsuji, et al., "Effects of L–156,602, a C5a Receptor Antagonist, on Mouse Experimental Models of Inflammation", Biosci., Biotech, Biochem., 56 (12), 2034–2036, 1992.
Fairlie, et al., "Macrocyclic Peptidomimetrics—Forcing Peptides into Bioactive Conformations", Curr. Med. Chem. (1995) 2:654–666.

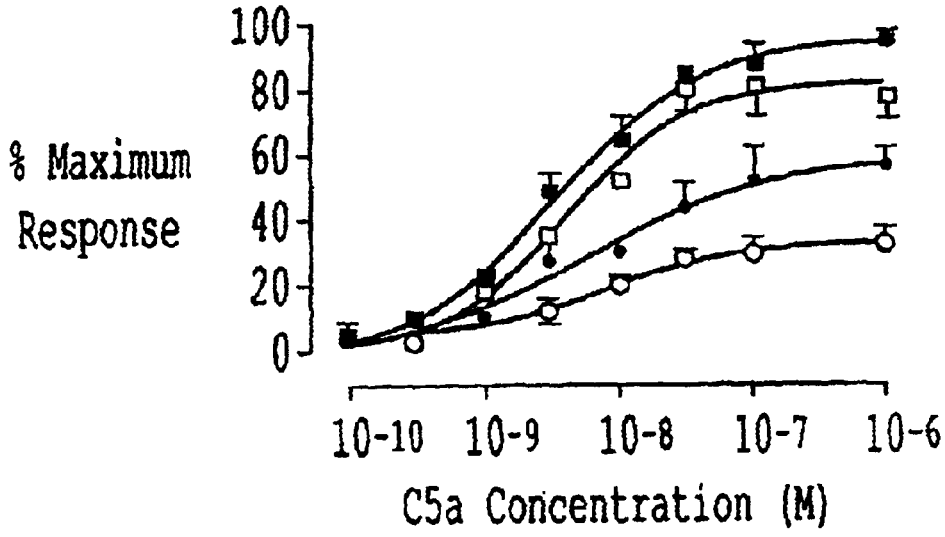
FIG. 5c(1)
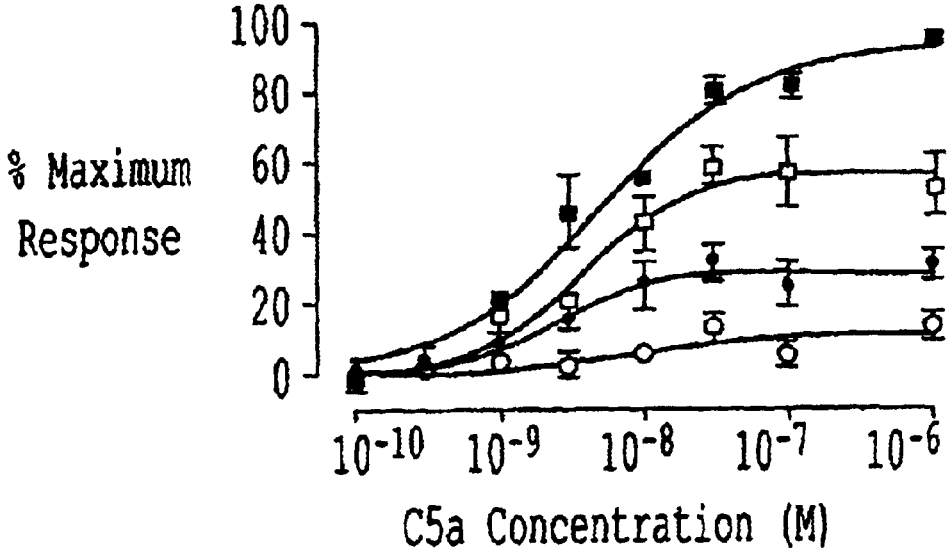
FIG. 5c(2)

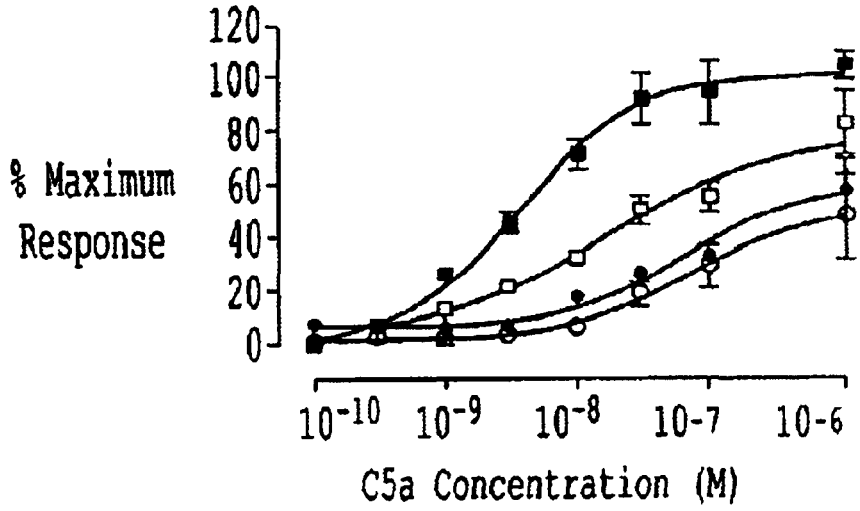
FIG. 5c(3)
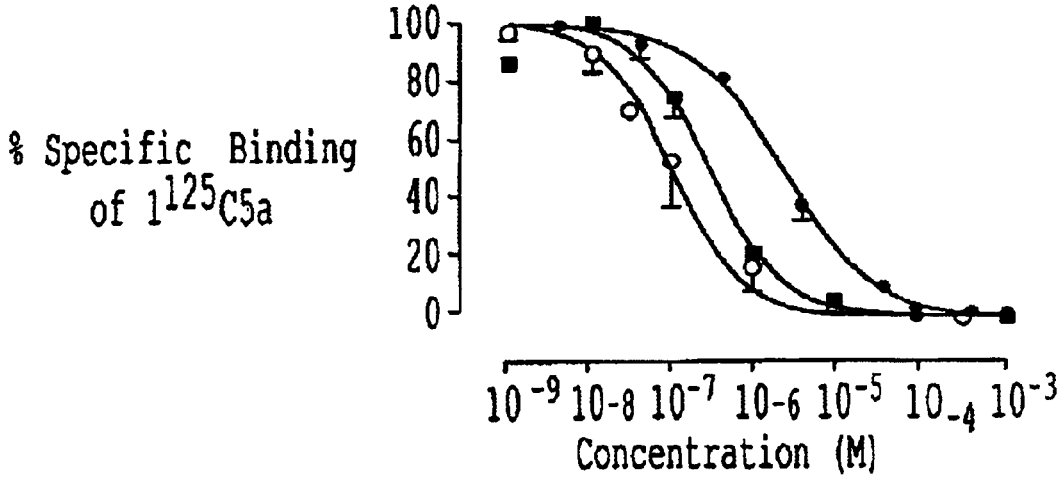
FIG. 5c(4)

CYCLIC AGONISTS AND ANTAGONISTS OF C5A RECEPTORS AND G PROTEIN-COUPLED RECEPTORS

Matter enclosed in heavy brackets [ ] appears in the original patent but forms no part of this reissue specification; matter printed in italics indicates the additions made by reissue.

This invention relates to novel cyclic compounds which have the ability to modulate the activity of G protein-coupled receptors. The invention provides both agonists and antagonists. In preferred embodiments, the invention provides cyclic peptidic and cyclic or non-cyclic non-peptidic antagonists or agonists of C5a. The compounds of the invention are both potent and selective, and are useful in the treatment of a variety of inflammatory conditions.

BACKGROUND OF THE INVENTION

Activation of human complement, a system of plasma proteins involved in immunological defence against infection and injury, contributes significantly to the pathogenesis of numerous acute and chronic diseases. In particular, the complement protein C5a has been extensively investigated. For general reviews, see Whaley (1987), and Sim (1993). Table 1 provides a summary of known roles of C5a in disease.

During host defence, the complement system of plasma proteins initiates inflammatory and cellular immune responses to stimuli such as infectious organisms (bacteria, viruses, parasites), chemical or physical injury, radiation or neoplasia. Complement is activated through a complex cascade of interrelated proteolytic events that produce multiple bioactive peptides, some of which (eg. anaphylatoxins C3a and C5a) interact with cellular components to propagate inflammatory processes. Complement activation, either by the classical pathway, after antigen-antibody (Ag/Ab) binding, or by the antibody-independent alternate pathway, ends with a terminal sequence in which protein C5 is proteolytically cleaved by C5 convertase to C5a and C5b. The latter facilitates assembly of a "membrane attack complex" that punches holes in membranes of target cells such as bacteria, leading to leakage, lysis and cell death. Steps in the cascade are tightly regulated to avoid stepwise amplification of proteolysis by sequentially formed proteases. If these regulatory mechanisms become inefficient, protracted activation of complement can result, causing enhanced inflammatory responses as in autoimmune diseases.

Although the broad features of the complement system and its activation are known, mechanistic details remain poorly understood. A principal and very potent mediator of inflammatory responses is the plasma glycoprotein C5a, which interacts with specific surface receptors (C5aR) on mast cells, neutrophils, monocytes, macrophages, non-myeloid cells, and vascular endothelial cells (Gerard and Gerard, 1994). C5aR is a G protein-coupled receptor with seven transmembrane helices (Gerard and Gerard, 1991). This receptor is one of the rhodopsin superfamily of GTP-linked binding proteins, but differs from rhodopsin receptors in that the receptor and G protein are linked prior to activation.

G protein-coupled receptors are prevalent throughout the human body, comprising approximately 80% of known cellular receptor types, and mediate signal transduction across the cell membrane for a very wide range of endogenous ligands. They participate in a diverse array of physiological and pathophysiological processes, including, but not limited to those associated with cardiovascular, central and peripheral nervous system, reproductive, metabolic, digestive, immunoinflammatory, and growth disorders, as well as other cell-regulatory and proliferative disorders. Agents, both agonists and antagonists, which selectively modulate functions of G protein-coupled receptors have important therapeutic applications.

C5a is one of the most potent chemotactic agents known, and results neutrophils and macrophages to sites of injury, alters their morphology; induces degranulation; increases calcium mobilisation, vascular permeability (oedema) and neutrophil adhesiveness; contracts smooth muscle; stimulates release of inflammatory mediators (including histamine, TNF-α, IL-1, IL-6, IL-8, prostaglandins, leukotrienes) and lysosomal enzymes; promotes formation of oxygen radicals; and enhances antibody production (Gerard and Gerard, 1994). Overexpression or underregulation of C5a is implicated in the pathogenesis of immunoinflammatory conditions such as rheumatoid arthritis, adult respiratory distress syndrome (ARDS), systemic lupus erythematosus, tissue graft rejection, ischaemic heart disease, reperfusion injury, septic shock, psoriasis, gingivitis, atherosclerosis, Alzheimer's disease, lung injury and extracorporeal post-dialysis syndrome, and in a variety of other conditions, as summarised in Table 1.

TABLE 1

The Role of C5a in Disease

| Condition/disease | C5a levels | C5aR expression | Details |
|---|---|---|---|
| allergy | ++ | | allergen challenge leads to nasal symptoms and increased C5a levels |
| Alzheimer's disease | ++ | ++ | up-regulation of the receptor in reactive astrocytes, microglia and endothelial cells in the CNS, complement system activated by β-amyloid |
| ARDS/respiratory distress | ++ | | |
| Behcet's disease | ++ | | levels highest just prior to ocular attacks |
| bronchial asthma | ++ | | |
| capillary leak syndrome | ++ | | |
| chronic lung disease | ++ | | Increased C5a levels in pulmonary effluent fluid from mechanically ventilated infants with chronic lung disease |
| Churg-Strauss | | | hypersensitivity of granulocytes to C5a |
| cystic fibrosis | | | generation of C5a/effects on PMNs |
| decompression stress | ++ | | increased C5a levels during saturation diving |
| diabetes type I | ++ | | C5a generated during onset; circulating monocytes in newly diagnosed type I diabetes patients are activated |
| Familial Mediterranean fever | | | Lack of C5a inactivator |
| Guillain-Barre | ++ | | CSF levels elevated |
| ischaemic disease states/myocardial infarct | | | migration of monocytes into myocardium after reperfusion. Damage prevented with sCR1 |
| Kimura's disease | | | humoral factor up-regulates the response of PMNs to C5a |
| Multiple Sclerosis | | ++ | increased expression of the receptor on foamy macrophages in acute and chronic MS and fibrous astrocytes in chronic MS |
| Meningitis | | | C5a induces experimental meningitis; PMN accumulation seen in the CSF |

TABLE 1-continued

The Role of C5a in Disease

| Condition/disease | C5a levels | C5aR expression | Details |
|---|---|---|---|
| pancreatitis | ++ | | |
| post-dialysis syndrome | ++ | – | C5a generated via complement activation by tubing material, C5aR levels decreased on PMNs & monocytes in chronic state |
| preeclampsin/ HELLP | ++ | | C5a levels in elevated at delivery |
| psoriasis | ++ | | C5a levels high in scales |
| reperfusion injury | ++ | | inhibited by C5 antibody |
| retinitis | ++ | | C5a detected in vitreous humor |
| Rheumatoid arthritis | ++ | | elevated concentration of C5a found in synovial fluid (5-fold) and plasma (3-fold) |
| Severe congenital neutropenia | | – | |
| transplant/graft rejection | ++ | | monoclonal antibodies block the damage seen with xenogenic transplant; increased levels of C5a seen in the plasma and urine of patients with renal graft rejection |

New agents which limit the pro-inflammatory actions of C5a have potential for inhibiting chronic inflammation, and its accompanying pain and tissue damage. For these reasons, molecules which prevent C5a binding to its receptors are useful for treating chronic inflammatory disorders driven by complement activation. Importantly, such compounds provide valuable new insights to mechanisms of complement-mediated immunity.

In another context, agonists of C5a receptors or other G protein-coupled receptors may also be found to have therapeutic properties in conditions either where the G protein-coupled receptor can be used as a recognition site for drug delivery, or where triggering of such receptors can be used to stimulate some aspect of the human immune system, for example in the treatment of cancers, viral or parasitic infections.

One approach to the development of agonists or antagonists of C5a is through receptor-based design, using knowledge of the three-dimensional structures of C5a, its receptor C5aR, and the interactions between them. The structure of the receptor is unknown. The solution structure of human C5a, a 74 amino acid peptide that is highly cationic and N-glycosylated with a 3 KDa carbohydrate at Asn64, has been determined and is essentially a 4-helix bundle. The C-terminal end (residues 65–74, $C5a_{65-74}$) was found to be unstructured (Zuiderweg et al, 1989) and this conformational flexibility in the C-terminus has made structure-function studies extremely difficult to interpret.

C5a has a highly ordered N-terminal core domain (residues 1–64; $C5a_{1-64}$), consisting of a compact antiparallel 4-helix bundle (residues 4–12, 18–26, 32–39, 46–63) connected by loops (13–17, 27–31, 40–45), and further stabilised by 3 disulphide bonds (C21-Cys47, Cys22–Cys54, Cys34–Cys55).

Although the structure of the C5a receptor, C5aR, is unknown, the C5a-binding subunit of human monocyte-derived C5aR has been cloned and identified as a G protein-coupled receptor with transmembrane helices (Gerard and Gerard, 1991). Interactions between C5a and C5aR have been the subject of many investigations which, in summary, suggest that C5a binds via a two-site mechanism in which the N-terminal core domain of C5a is involved in receptor-recognition and binding, while the C-terminus is responsible for receptor activation. This mechanism is illustrated schematically in FIG. 1. The C-terminal "effector" region alone possesses all the information necessary for signal transduction, and is thought to bind in the receptor's interhelical region (Siciliano et al, 1994; deMartino et al, 1995).

An N-terminal interhelical positively-charged region of C5a is responsible for receptor recognition and binding, and binds to a negatively-charged extracellular domain of C5aR (site 1), while the C-terminal "effector" region of C5a is thought to bind with the interhelical region of the receptor (site 2), and is responsible for receptor activation leading to signal transduction (Siciliano et al, 1994).

Numerous short peptide derivatives of the C-terminus of C5a have been found to be agonists of C5a (Kawai et al, 1991; Kawai et al, 1992; Kohl et al, 1993; Drapeau et al, 1993; Ember et al, 1992; Sanderson et al, 1994; Sanderson et al, 1995; Finch et al, 1997; Tempero et al, 1997; Konteatis et al, 1994; DeMartino et al, 1995). The structures of some of these agonists are shown in Table 2 below (compounds 1–6). High molecular weight polypeptide inhibitors of the action of C5a at its receptor, such as monoclonal antibodies to the C5a receptor, are also known (Morgan et al, 1992).

A small molecule, N-methylphenylalanine-lysine-proline-D-cyclohexylalanine-tryptophan-D-arginine (7, MeF-K—P-dCha-W—R), is a full antagonist of the C5a receptor, with no agonist activity when tested on isolated cellular membranes (Konteatis et al, 1994) or intact whole cells. This hexapeptide was developed by modifications of the agonist NMe-F—K—P-dCha-L-r, in which the molecule was progressively substituted at leucine residues with substituents of increasing size (Cha, F, Nph and W). This had the effect of reducing agonist activity. Receptor-binding assays, performed on isolated human neutrophil membranes, showed that the antagonist had only 0.04% relative affinity of C5a for the receptor (Konteatis et al, 1994). A key feature of these reports is the definition of the binding of 7 to the C5a receptor. These authors state that the C-terminal arginine is essential for receptor binding and antagonist activity. This is also the case in all the reports of agonist activity by small peptide analogues of the C-terminus of C5a. However, for the antagonist 7, the authors go further and state that "the C-terminal carboxylate is an essential requirement for antagonist activity and receptor binding."

They proposed that the requirement of the carboxylate is probably the result of its specific interaction with an arginine (Arg 206) in the receptor (De Martino et al, 1995). This idea was supported by a great reduction in receptor-affinity for an analogue of 7 in which the D-arginine ($NH_2$—$CH(CO_2H)$—$(CH_2)_3NHC(:NH)NH_2$) was replaced by agmatine ($NH_2$—$CH_2$—$(CH_2)_3NHC(:NH)NH_2$). In summary, De Martino et al claim that the D-arginine interacts via its guanidinium side chain with a negatively-charged amino acid side chain in the receptor. A second interaction between the negatively-charged C-terminal carboxylate of 7 and a positively-charged side chain residue in the receptor is also thought to occur.

We have now determined the solution structure of this hexapeptide 7 and several analogues, and have surprisingly found that in fact a terminal carboxylate group is not required for binding to C5aR or for antagonist activity, and that instead an unusual hitherto unrecognised structural feature, a turn conformation, is responsible for C5a antagonist or agonist binding and activity. The hexapeptide and several new structurally related antagonists have been examined for both their receptor-binding affinities and antagonist activity, using intact polymorphonuclear (PMN) cells. Our results show the hitherto unknown specific structural requirement for the binding of C5a antagonists or agonists to the C5a receptor, which we believe to be common to ligands for the G protein-coupled receptor family. Our establishment of this specific structural requirement has enabled us to design and develop improved molecular probes of the complement system and of C5a-based drugs, and to design small molecules that target other G protein-coupled receptors, which are becoming increasingly recognised as important drug targets due to their crucial roles in signal transduction (G protein-coupled Receptors, IBC Biomedical Library Series, 1996).

Thus our results have enabled us to design constrained structural templates which enable hydrophobic groups to be assembled into a hydrophobic array for interaction with a G protein-coupled receptor, for example at Site 2 of the C5a receptor illustrated in FIG. 1. Such templates or scaffolds, which may be cyclic or acyclic, have not heretofore been suggested for modulators of the activity of C5a receptors or other G protein-coupled receptors.

SUMMARY OF THE INVENTION

The invention provides cyclic and non-cyclic modulators of the activity of G-protein-coupled receptors.

According to a first aspect, the invention provides a compound which is an antagonist, of a G protein-coupled receptor, which has no agonist activity, and which has a cyclic or constrained acyclic structure adapted to provide a framework of approximate dimensions as follows:

Structure I

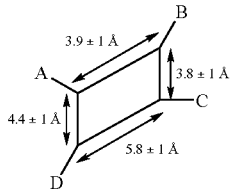

where the numerals refer to distances between $C_n$ carbons of amino acids or their analogues or derivatives, and A, B, C and D are not necessarily on adjacent amino acids, or analogues or derivatives thereof; and where the critical amino acid side chains are designated by A, B, C and D, or are as defined below;

A is any common or uncommon, basic, charged amino acid side chain which serves to position a positively charged group in this position, including, but not limited to the following side chains and other mimetics of arginine side chains:

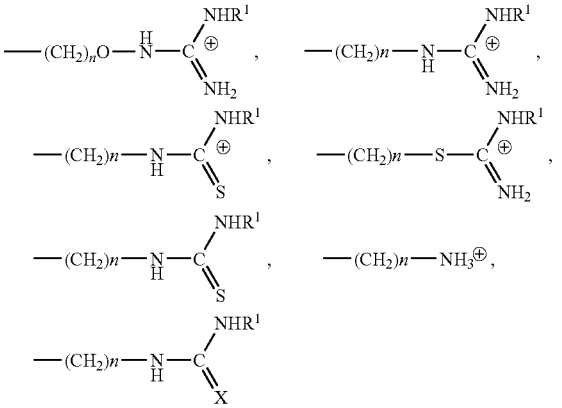

where

X is NCH, $NNO_2$, $CHNO_2$ or $NSO_2NH_2$;

n is an integer from 1 to 4, and

R is H or an alkyl, aryl, CN, $NH_2$ or OH group

B is any common or uncommon aromatic amino acid side chain which serves to position an aromatic side-chain group in this position, including but not limited to the indole, indole methyl, benzyl, phenyl, naphthyl, naphthyl methyl, cinnamyl group, or any other derivatives of these aromatic groups;

C is any common or uncommon hydrophobic amino acid side chain which serves to position any alkyl, aromatic or other group in this position, including, but not limited to D- or L-cyclohexyl alanine (Cha), leucine, valine, isoleucine, phenylalanine, tryptophan, or methionin D is any common or uncommon aromatic amino acid which serves to position an aromatic side-chain in this position, and has the structure:

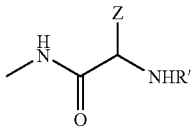

where Z includes but is not limited to indole, indole methyl, benzyl, benzene, naphthyl, naphthyl methyl, or any other derivatives of these aromatic groups, and $R^1$ is H or any alkyl, aromatic, acyl or aromatic-acyl group including, but not limited to methyl, ethyl, propyl, butyl, —CO—$CH_2CH_3$, —CO—$CH_3$, —CO—$CH_2CH_2CH_3$, —CO—$CH_2$Ph, or —CO-Ph.

Preferably the G protein-coupled receptor is a C5a receptor.

Other cyclic or constrained acyclic molecules, which may be peptidic or non-peptide in nature, can similarly be envisaged to support groups such as A, B, C and D for interaction with a C5a receptor or other G protein-coupled receptor.

In one preferred embodiment, the compound has antagonist activity against C5aR, has no C5a agonist activity, and has the general formula:

Structure II

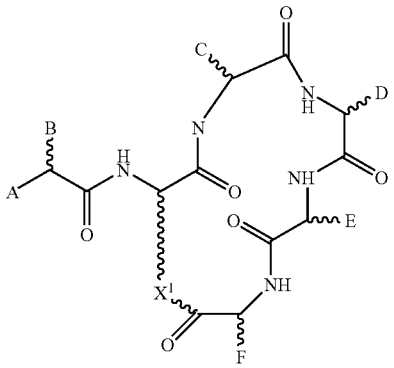

where A is H, alkyl, aryl, $NH_2$, NHalkyl, $N(alkyl)_2$, NHaryl or NHacyl; OH, Oalkyl, Oaryl.

B is an alkyl, aryl, phenyl, benzyl, naphthyl or indole group, or the side chain of a D- or L-amino acid selected from phenylalanine, homophenylalanine, tryptophan, homotryptophan, tyrosine, and homotyrosine;

C is the side chain of a D-, L- or homo-amino acid selected from the group consisting of proline, alanine, leucine, valine, isoleucine, arginine, histidine, aspartate, glutamate, glutamine, asparagine, lysine, tyrosine, phenylalanine, cyclohexylalanine, norleucine, tryptophan, cysteine and methionine;

D is the side chain of a D- or L-amino acid selected from the group consisting of cyclohexylalanine, homocyclohexylalanine, leucine, norleucine, homoleucine, homonorleucine and tryptophan;

E is the side chain of a D- or L-amino acid selected from the group consisting of tryptophan and homotryptophan;

F is the side chain of a D- or L-amino acid selected from the group consisting of arginine, homoarginine, lysine and homolysine; and $X^1$ is —$(CH_2)_n$NH— or $(CH_2)_n$—S—, where n is an integer of from 1 to 4, preferably 2 or 3, —$(CH_2)_2$O—, —$(CH_2)_3$O—, —$(CH_2)_3$—, —$(CH_2)_4$—, or —$CH_2$COCHRNH—, where R is the side chain of any common or uncommon amino acid.

For the purposes of this specification, the term "alkyl" is to be taken to mean a straight, branched, or cyclic, substituted or unsubstituted alkyl chain of 1 to 6, preferably 1 to 4 carbons. Most preferably the alkyl group is a methyl group. The term "acyl" is to be taken to mean a substituted or unsubstituted acyl of 1 to 6, preferably 1 to 4 carbon atoms. Most preferably the acyl group is acetyl. The term "aryl" is to be understood to mean a substituted or unsubstituted homocyclic or heterocyclic aryl group, in which the ring preferably has 5 or 6 members.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine.

An "uncommon" amino acid includes, but is not restricted to, D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, γ-glutamic acid, aminobutyric acid and α,α-disubstituted amino acids.

For the purposes of this specification it will be clearly understood that the word "comprising" means "including but not limited to", and that the word "comprises" has a corresponding meaning.

According to a second aspect, of the invention provides a compound which is an agonist of G protein-coupled receptors, and which has structure III Structure III

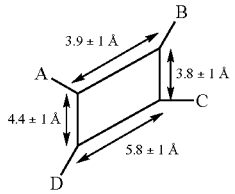

where the numerals refer to distances between $C_n$ carbons of amino acids or their analogues or derivatives, and A, B, C and D are not necessarily on adjacent amino acids, or analogues or derivatives thereof; and where B is a non-aromatic amino acid, and is preferably the D- or L-form of alanine, leucine, valine, norleucine, glutamic acid, aspartic acid, methionine, cysteine, isoleucine, serine or threonine, and A, C and D are as defined above.

Preferably the compound is of structure IV,

Structure IV

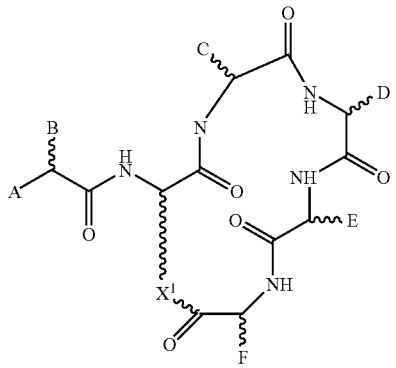

where E is any amino acid other than tryptophan and homotryptophan, for example D- or L-forms of alanine, leucine, valine, norleucine, phenylalanine, glutamic acid, aspartic acid, methionine, cysteine, isoleucine, serine, threonine, and F and $X^1$ are as defined in Structure II. Preferably the compound is an agonist of C5a.

According to a third aspect, the invention provides a composition, comprising a compound according to the invention together with a pharmaceutically-acceptable carrier or excipient.

The compositions of the invention may be formulated for oral or parenteral use, but oral formulations are preferred. It is expected that most if not all compounds of the invention will be stable in the presence of digestive enzymes. Such stability can readily be tested by routine methods known to those skilled in the art.

Suitable formulations for administration by any desired route may be prepared by standard methods, for example by reference to well-known textbooks such as Remington; The Science and Practice of Pharmacy, Vol. II, 1995 ($19^{th}$ edition), A. R. Gennaro (ed), Mack Publishing Company, Easton, Pa., or Australian Prescription Products Guide, Vol. 1, 1995 ($24^{th}$ edition) J. Thomas (ed), Australian Pharmaceutical Publishing Company Ltd, Victoria, Australia.

In a fourth aspect, the invention provides a method of treatment of a pathological condition mediated by a G protein-coupled receptor, comprising the step of administering an effective amount of a compound of the invention to a mammal in need of such treatment.

Preferably the condition mediated by a G protein-coupled receptor is a condition mediated by a C5a receptor, and more preferably involves overexpression or underregulation of C5a. Such conditions include but are not limited to rheumatoid arthritis, adult respiratory distress syndrome (ARDS), systemic lupus erythematosus, tissue graft rejection, ischaemic heart disease, reperfusion injury, septic shock, psoriasis, gingivitis, atherosclerosis, Alzheimer's disease, lung injury and extracorporeal post-dialysis syndrome.

While the invention is not in any way restricted to the treatment of any particular animal or species, it is particularly contemplated that the compounds of the invention will be useful in medical treatment of humans, and will also be useful in veterinary treatment, particularly of companion animals such as cats and dogs, livestock such as cattle, horses and sheep, and zoo animals, including large bovids, felids, ungulates and canids.

The compounds may be administered at any suitable dose and by any suitable route. Oral administration is preferred because of its greater convenience and acceptability. The effective dose will depend on the nature of the condition to be treated, and the age, weight, and underlying state of health of the individual treatment. This will be at the discretion of the attending physician or veterinarian. Suitable dosage levels may readily be determined by trail and error experimentation, using methods which are well-known in the art.

BRIEF DESCRIPTION OF THE FIGURES

FIG. 5c shows C5aR binding and antagonist potencies of 7, 15 and 17.

A–C show the effect of increasing concentrations (top to bottom) of C5a antagonists inhibiting myeloperoxidase release in human PMNs (n=3 in A–C).

A: 7 at 0, 0.1, 0.3, 1.0 μM (top to bottom)

B: 15 at 0, 0.1, 0.03, 0.1 μM (top to bottom)

C: 17 at 0, 0.01, 0.03, 0.1 μM (top to bottom)

D: Comparative affinities for PMN C5qR receptor. Inhibition of binding of $^{125}$I-C5a to human PMNs by 7 (top), (middle), 17 (bottom). All data are means±SEM.

Figure 6:
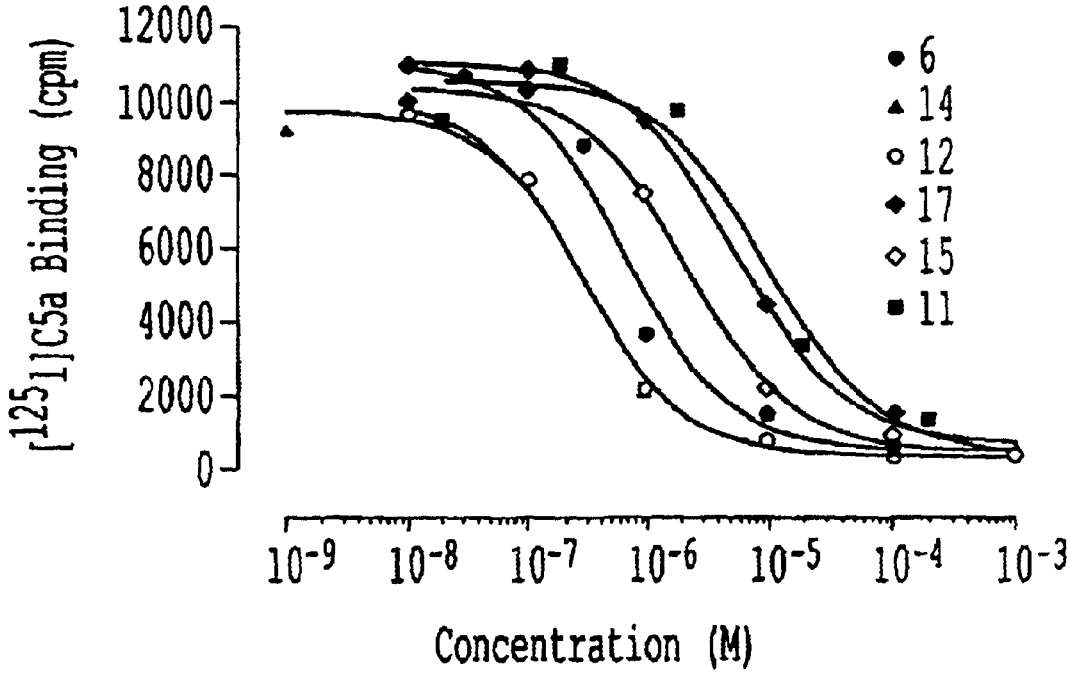

FIG. 6 shows receptor binding of cyclic C5a antagonists, as-shown by inhibition of binding of $^{125}$I-C5a to human PMNs (n=5).

Figure 7:
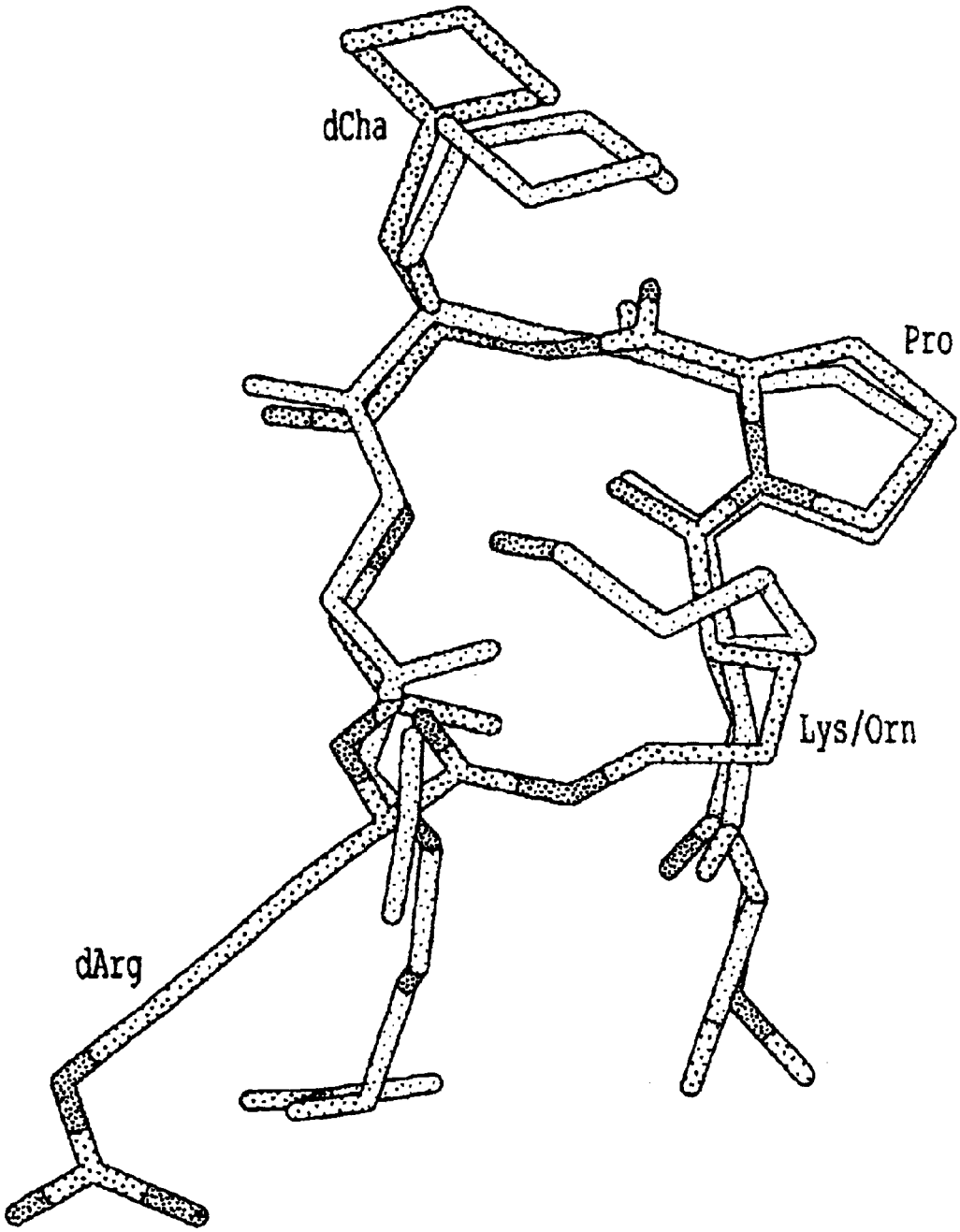

FIG. 7 shows superimposed structures of 7 (light, NMR structure) and 12 (dark, computer modelled structure). Phe and Trp side chains are omitted from 12 for clarity.

Figure 8:
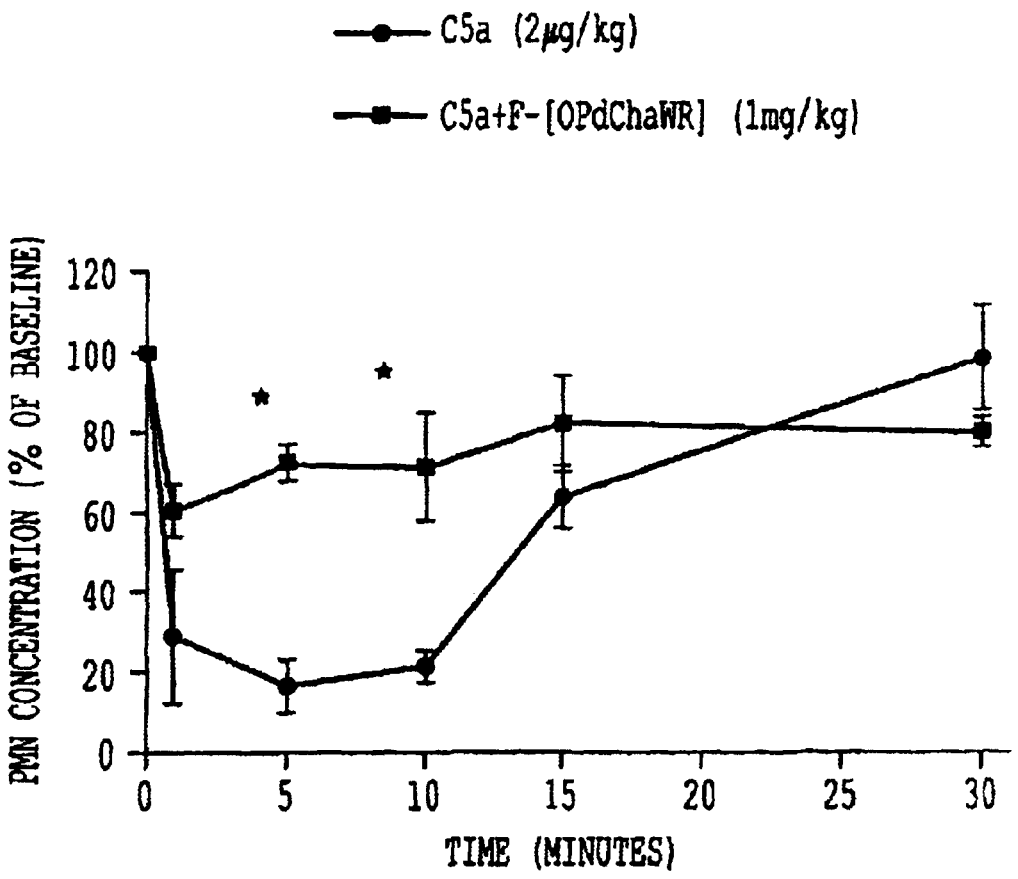

FIG. 8 shows inhibition of C5a-induced neutropenia in Wistar rats by the cyclic antagonist F-[OPdChaWR] given i.v. at 1 mg/kg. Results shown from n=3 in each group, *P<0.05 compared to C5a-treated group only. Results are expressed as means±SEM.

Figure 9A:
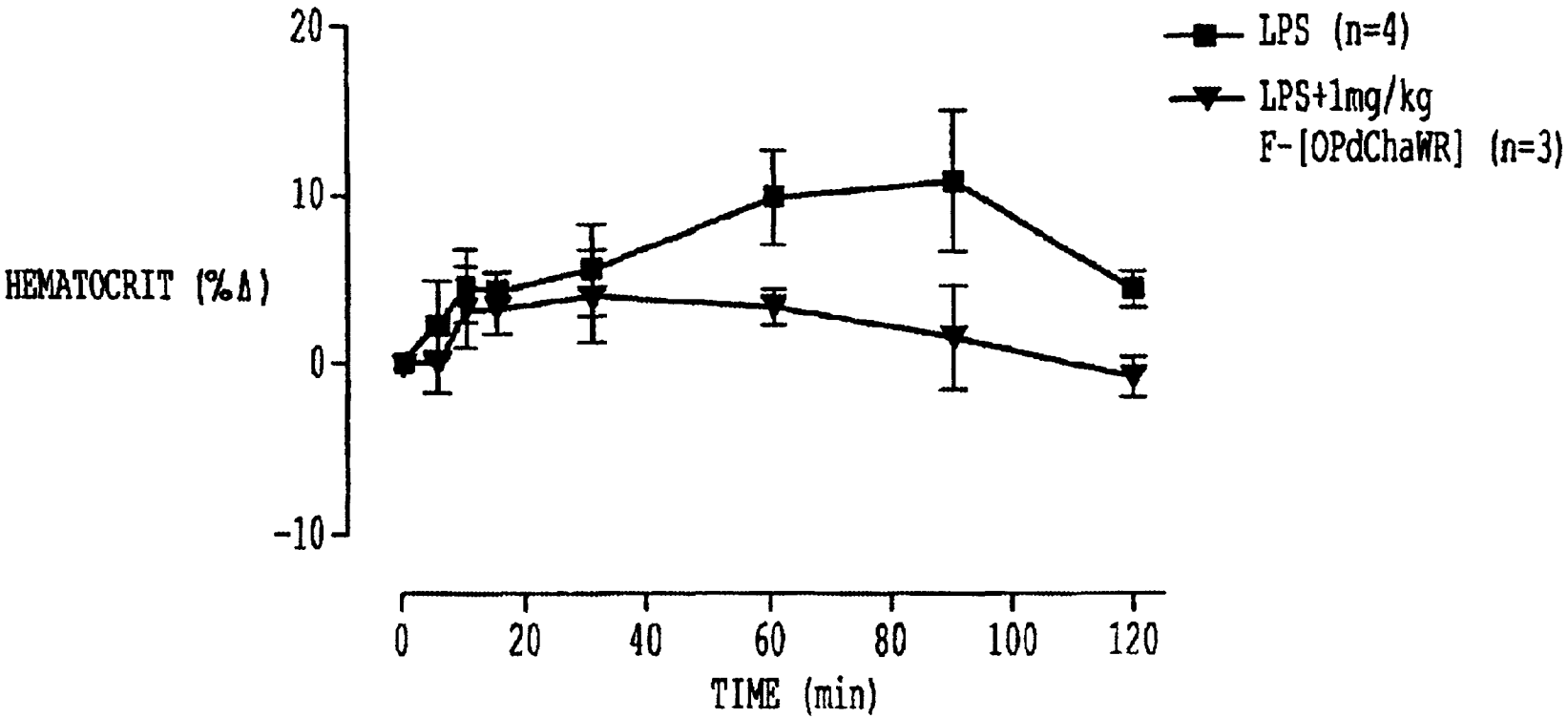
Figure 9B:
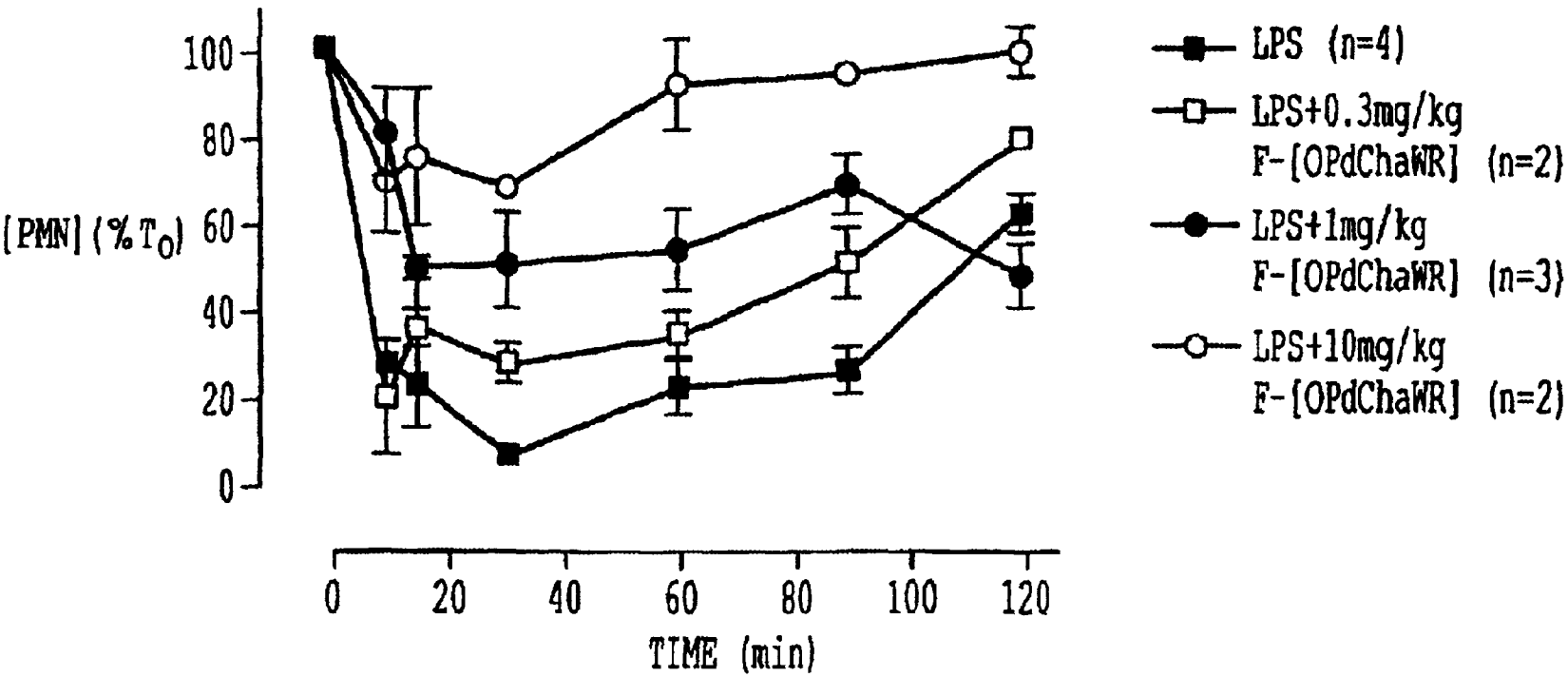

FIG. 9 shows inhibition of LPS-induced neutropenia and changes in haematocrit induced by the cyclic antagonist F-[OPdChaWR] (0.03–10 mg/kg, i.v., 10 min prior to lipopolysaccharide [LPS]) in Wistar rats.
Abscissa: time after LPS (1 mg/kg i.v. injection).
Ordinate: percent change in haematocrit (A) value or level of circulating polymorphonuclear (PMN) leukocytes (B) compared to time zero.

Figure 10:
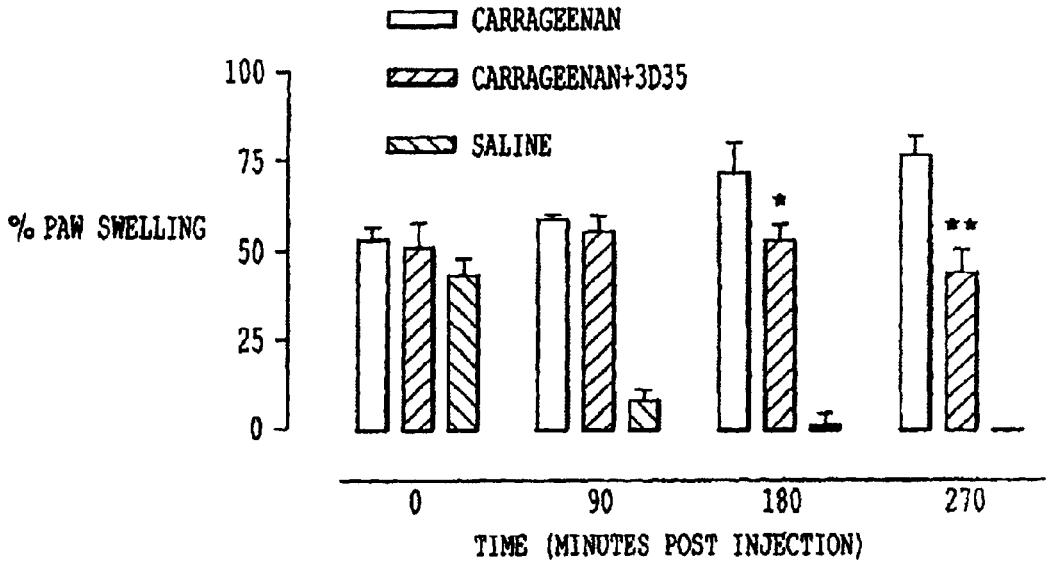

FIG. 10 shows inhibition of carrageenan-induced (Wistar) rat paw oedema by cyclic antagonist (3D35) AcF-[OPdChaWr] (1 mg/kg single dose i.p. given 30 min prior to carrageenan). Results shown from 4 rats/group, means±SEM. Ordinate: percent change in paw volume. Abscissa: time (mins) after carrageenan injection

DETAILED DESCRIPTION OF THE INVENTION

The invention will now be described by way of reference only to the following general methods and experimental examples, and to the figures. Abbreviations used herein are as follows:

| | |
|---|---|
| BOP | benzotriazole-1-yl-oxy-tris-(dimethylamino)-phosphonium hexafluorophosphate |
| D-Cha | D-cyclohexylamine |
| DIPEA | diisopropylethylamine |
| DMF | dimethylformamide |
| DMSO | dimethylsulphoxide |
| HBTU | O-benzotriazole N',N',N',N'-tetramethyluronium hexafluorophosphate |
| LPS | lipopolysaccharide |
| PMN | polymorphonuclear granulocyte |
| RMSD | root mean square deviation |
| RP-HPLC | reverse phase-high performance liquid chromatography |
| TFA | trifluoroacetic acid; |

Throughout the specification conventional single-letter and three-letter codes are used to represent amino acids.

General Methods

Protected amino acids and resins were obtained from Novabiochem. TFA, DIPEA and DMF (peptide synthesis grade) were purchased from Auspep. All other materials were reagent grade unless otherwise stated. Preparative scale reverse-phase HPLC separations were performed on a Vydac C18 reverse-phase column (2.2×25 cm), and analytical reverse-phase HPLC separations were performed on a waters Delta-Pak PrepPak C18 reverse-phase column (0.8×10 cm), using gradient mixtures of solvent A=water/0.1% TFA and solvent B=water 10%/acetonitrile 90%, 0.09% TFA. The molecular weight of the peptides was determined by electrospray mass spectrometry recorded on a triple quadrupole mass spectrometer (PE SCIEX API III), as described elsewhere (Haviland et al, 1995). $^{1}$H-NMR spectra were recorded on either a Bruker ARX 500 MHz or a Varian Unity 400 spectrometer. Proton assignments were determined by 2D NMR experiments (DFCOSY, TOCSY, NOESY).

Non-peptidic compounds were synthesized using conventional organic chemical methods. Compounds were analysed by $^{1}$H-NMR spectroscopy and by mass spectrometry.

Peptide Synthesis

Some representative peptide syntheses are now given. Linear peptide sequences were assembled by manual stepwise solid-phase peptide synthesis with HBTU activation and DIEA in situ neutralisation. Boc chemistry was employed for temporary $N^{\alpha}$-protection of amino acids with two 1 min treatments with TFA for Boc group removal. The peptides were fully deprotected and cleaved by treatment with liquid HF (10 ml; p-cresol (1 ml); −5° C.; 1–2 hr). Analytical HPLC (gradient; 0% B to 50% B over 40 min); 7, Rt=32.0 min, $[M+H]^+$(calc.)=900.5, $[M+H]^+$(exper.)=900.7; 8, Rt=32.2 min, $[M+H]^+$(calc.)=899.6, $[M+H]^+$(exper.)=899.7; 9, Rt=30.0 min, $[M+H)^+$(calc.)=900.5, $[M+H]^+$(exper.)=900.7; 10, Rt=23.8 min, $[M+H]^+$(calc.)=860.5, $[M+H]^+$(exper.) 860.5.

Structures for the peptides are shown in Table 4 below.

a) Synthesis of Cycle 11

This is a general method used for the synthesis of a wide range of cyclic antagonists covered by this patent. For example, in the case of cycle 11, its linear precursor peptide was synthesised by Fmoc chemistry using HBTU/DIEA activation on an Fmoc-D-Arg(Mtr)-Want resin. Fmoc group removal was effected using two 1 min treatments with 50% piperidine/DMF. Cleavage and deprotection using 95% TFA/2.5% TIPS/2.5% $H_2O$ gave the Mtr-protected peptide, which was purified by RP-HPLC. Cyclization of the protected, purified peptide using 3eq BOP and 10eq DIEA at a 1 mM concentration in DMF stirring for 15 hr gave the cyclised product, which was fully deprotected using 1M TMSBr in TFA. A final RP-HPLC purification gave the desired peptide in yields of 50% for the cyclisation. Rt=37.7 min, $[M+H]^+$(calc.) 910.5, $[M+H]^+$(exper.)=910.7.

b) Synthesis of Cycle 12

Cyclization of the cleaved and fully deprotected peptide was achieved by stirring a 1 mM solution in DMF with 3eq BOP and 10 eq pyridine as base for 15 hr. A final RP-HPLC purification gave the desired peptide in yields of 22% for the cyclization. Rt=37.3 min, (M+H]+(calc.)=896.5, [M+H]+(exper.)=896.5.

NMR Structure Determination $^1$H-NMR spectra were recorded for compound 7 (3 mg in 750 μl $d_6$-DMSO, δ2.50) referenced to solvent on a Varian Unity 400 spectrometer at 24° C. Two dimensional $^1$H-NMR NOESY (relaxation delay 2.0 s, mix time 50–300 ms), DFQ-COSY and TOCSY (mixing time 75 ms) experiments were acquired and recorded in phase sensitive mode. Acquisition times=0.186 s, spectral width=5500 Hz, number of complex points ($t_1$ dimension)=1024 for all experiments. Data was zero-filled and Fourier transformed to 1024 real points in both dimensions.

NMR data was processed using TRIAD software (Tripos Assoc.) on a Silicon Graphics Indy work station. 2D NOE cross peaks were integrated and characterised into strong (1.8–2.5 Å), medium (2.3–3.5 Å) and weak (3.3–5.0 Å). Preliminary three-dimensional structures were calculated from upper and lower distance limit files using Diana 2.8 (69 distance constraints, including 27 for adjacent residues and 6 further away) with the redundant dihedral angle constraints (REDAC) strategy. Upper and lower distance constraints were accurately calculated using MARDIGRAS. At this stage the peptide was examined for possible hydrogen bonds, and these were added as distance constraints. The 50 lowest energy Diana structures were subjected to restrained molecular dynamics (RMD) and energy minimisation (REM). Initially, REM consisted of a 50 step steepest descent followed by 100 step conjugate gradient minimisation. RMD was performed by simulated heating of the structures to 300K for 1 ps, followed by 500K for 1 ps. The temperature was gradually lowered to 300K over 2 ps and finally for 2 ps at 200K. REM was performed again with a 50 step steepest descent, 200 step conjugate gradient followed by a 300 step Powell minimisation. The final structures were examined to obtain a mean pairwise rms difference over the backbone heavy atoms (N, Cα and C). Twenty of the 50 structures had a mean rmsd<0.5 Å for all backbone atoms (O, N, C).

Molecular Modelling

A model of cycle 12, shown in FIG. 7, was created from the NMR structure of 7 by deleting all NMR constraints, fusing the ornithine side chain amine to the C-terminal carboxylate of d-Arg to form an amide, and minimising using Powell forcefield (1000 iterations). The modelled structure was then superimposed on the NMR structure with an rmsd 0.224 Å.

Receptor-Binding Assay

Assays were performed with fresh human PMNs, isolated as previously described (Sanderson et al, 1995), using a buffer of 50 mm HEPES, 1 mM $CaCl_2$, 5 mM $MgCl_2$, 0.5% bovine serum albumin, 0.1% bacitracin and 100 μM phenylmethylsulfonyl fluoride (PMSF). In assays performed at 4° C., buffer, unlabelled human recombinant C5a (Sigma) or peptide, Hunter/Bolton labelled $^{125}$, —C5a (~20 pM) (New England Nuclear, MA) and PMNs ($0.2\times10^6$) were added sequentially to a Millipore Multiscreen assay plate (HV 0.45) having a final volume of 200 μL/well. After incubation for 60 min at 4° C., the samples were filtered and the plate washed once with buffer. Filters were dried, punched and counted in an LKB gamma counter. Non-specific binding was assessed by the inclusion of 1 mM peptide or 100 nM C5a which typically resulted in 10–15% total binding.

Data was analysed using non-linear regression and statistics with Dunnett post test.

Myeloperoxidase Release

Cells were isolated as previously described (Sanderson et al, 1995) and incubated with cytochalasin B (5 μg/mL, 15 min, 37° C.). Hank's Balanced Salt solution containing 0.15% gelatin and peptide was added on to a 96 well plate (total volume 100 μL/well), followed by 25 μL cells ($4\times10^6$/mL). To assess the capacity of each peptide to antagonise C5a, cells were incubated for 5 min at 37° C. with each peptide, followed by addition of C5a (100 nM) and further incubation for 5 min. Then 50 μL of sodium phosphate (0.1M, pH 6.8) was added to each well, the plate was cooled to room temperature, and 25 μL of a fresh mixture of equal volumes of dimethoxybenzidine (5.7 mg/mL) and $H_2O_2$ (0.51%) was added to each well. The reaction was stopped at 10 min by addition of 2% sodium azide. Absorbances were measured at 450 nm in a Bioscan 450 plate reader, corrected for control values (no peptide), and analysed by non-linear regression.

In Vivo Assays of Anti-Inflammatory Activity

The following well-known in vivo assay systems may be used to assess the anti-inflammatory activity of compounds of the invention. All assay data are analysed using non-linear regression analysis and Student's t-test, analysis of variance, with $p<0.05$ as the threshold level of significance.

(a) Carrageenan Paw Oedema

Anaesthetised (i.p. ketamine & xylazine) Wistar rats (150–200 g) or mice were injected with sterilised air (20 ml day 1, 10 ml day 4) into the subcutaneous tissue of the back. The cavity can be used after 6 days, whereupon carrageenan (2 ml, 1% w/w in 0.9% saline) was injected into the air pouch and exudate was collected after 10 hr. Test compounds are administered daily after Day 6 and their anti-inflammatory effects assayed by differential counting of cells in the air-pouch exudate. Animals were killed at appropriate times after injection and 2 ml 0.9% saline was used to lavage the cavity, lavage fluids were transferred to heparinised tube and cells were counted with a haemocytometer and Diff-Quik strained cytocentrifuged preparation.

Alternatively, a routine carrageenan paw oedema was developed in Wistar rats by administering a pedal injection of carrageenan to elicit oedema which is visible in 2 h and maximised in 4 h. Test compounds are given 40 min before inflammagen and evaluated by microcaliper measurements of paws after 2 & 4 hr. See Fairlie, D. P. et al (1987). Also see Walker and Whitehouse (1978).

(b) Adjuvant Arthritis.

Adjuvant arthritis was induced in rats (3 strains) either microbially (injection of heat-killed Mycobacterium tuberculosis) or chemically (with pyridine) by inoculation with the arthritogenic adjuvant co-administered with oily vehicles (Freund's adjuvants) in the tail base. (See Whitehouse, M. W., Handbook of Animal Models for the Rheumatic Diseases, Eds. Greenwald, R. A.; Diamond, H. S.; Vol. 1, pp. 3–16, CRC Press).

Within 13 days the adjuvant arthritis is manifested by local inflammation and ulceration in the tail, gross swelling of all four paws, inflammatory lesions in paws and ears, weight loss and fever. These symptoms, which are similar to those of inflammatory disease in humans (Winter and Nuss, 1966), can be alleviated by agents such as indomethacin or cyclosporin which also show beneficial effects in man (eg. Ward and Cloud, 1966). Without drug treatment at Day 14, arthritic rats had hypertrophy of the paws, reduced albumin but raised acute phase reaction proteins in serum, and depressed hepatic metabolism of xenobiotics as indicated by prolonged barbiturate-induced sleeping times.

To assess activity, compounds were administered for 4 days orally (<10 mg/kg/day) or i.p. from Days 10–13 following inoculation with arthritogen (Day 0). The inflammation was either not visible or very significantly reduced in rear or front paws as assessed by microcaliper measurements of paw thickness and tail volume, as well as by gross inspection of inflammatory lesions. Animals are sacrificed by cervical dislocation on Day 18 unless arthritis signs are absent, whereupon duration of observations is continued with special permission from the Ethics committees. Experiments are staggered to maximise throughput and allow early comparisons between compounds. This routine assay is well-accepted as identifying anti-inflammatory agents for use in humans.

EXAMPLE 1

Structure-Activity Relationship of C5a Agonists

We have focused on the C-terminal residues of C5a, in order to explore structure-activity relationships in the search for peptide sequences with potent agonist activity. Many of these peptides are full agonists relative to C5a, but have markedly lower potency (Sanderson et al, 1994, 1995; Finch et al, 1997). Our initial structure-activity investigations have been particularly informative. Mutating the decapeptide C-terminus of C5a (SEQ ID NO: 1, $C5a_{65-74}$, ISHKDMQLGR) twice with $I_{65}Y$ and $H_{67}F$ (eg. 2) led to enhancement of agonist potency by about 2 orders of magnitude. These results are summarised in Table 2. Analyses of Ramschandran plots and 2D NMR spectra for compound 2 suggested that certain structural features, namely a twisted "helix-like" backbone conformation for residues 65–69 and a β-turn for residues 71–74, might be responsible for activity. These preliminary results provided some insight to structural requirements for tight binding to a C5a receptor.

TABLE 2

Pharmacological Activity of C5a Agonist Analogues*

| Peptide No. | Peptide | Fetal Artery $EC_{50}$ (μM) | PMN Enzyme Release $EC_{50}$ (μM) | Binding Affinity $IC_{50}$ (μM) |
|---|---|---|---|---|
| SEQ. ID NO: 1 | $C5a_{65-74}$ (ISHKDMQLGR) | >1000 | >1000 | >1000 |
| SEQ. ID NO: 2 | YSFKDMQLGR | 9.6 | 92 | 1.3 |
| SEQ. ID NO: 3 | YSFKDMPLaR | 0.5 | 72 | 3.7 |
| SEQ. ID NO: 4 | YSFKPMPLaR | 0.2 | 4.3 | 6.0 |
| SEQ. ID NO: 5 | $C5a_{37-46}$-ahxYSFKPMPLaR | 0.06 | 5.9 | 0.7 |
| SEQ. ID NO: 6 | $C5a_{12-20}$-ahxYSFKPMPLaR | 0.08 | 0.7 | 0.07 |
| | C5a | 0.02 | 0.03 | 0.0005 |

*Finch et al, 1997

Compounds 4, 5 and 6 in Table 2 are the highest affinity small C5a agonists so far known, with up to 25% C5a potency in human fetal artery, 5% C5potency in human PMN enzyme release assays and 1% C5a affinity for PMN C5aR (Finch et al., 1997). For the PMN receptor, these compounds have up to 100-fold higher apparent affinity than any small molecule previously described in the literature.

The "high" affinities (70 nM-6 μM) of these agonist analogues for C5aR in intact PMN cells have enabled us to identify a common topographical feature in peptide agonists that correlates with expression of spasmogenic activities and enzyme-release assays in human PMNs. This preferred backbone conformation is a type II β-turn.

The small size of these agonist peptides makes them amenable to synthetic modification to optimise their affinities, activities, and bioavailabilities, and hence useful as mechanistic probes of receptor activation.

EXAMPLE 2

NMR Structure of C5a Antagonist

We used two dimensional nuclear magnetic resonance spectroscopy to determine the three dimensional structure of 7 and found that while there is no discernible structure in water, there is evidence of a stable gamma-turn structure in dimethylsulfoxide.

Figure 1:
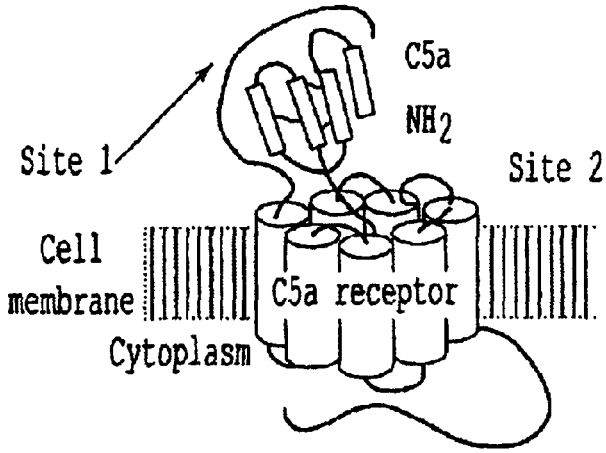
FIG. 1 shows a diagrammatic representation of the two-site model for binding of C5a to its G protein-coupled receptor, C5aR. The black rods represent a-helical regions, and the open cylinders represent the transmembrane helices. Sites 1 and 2 are indicated on the figure.
Figure 2:
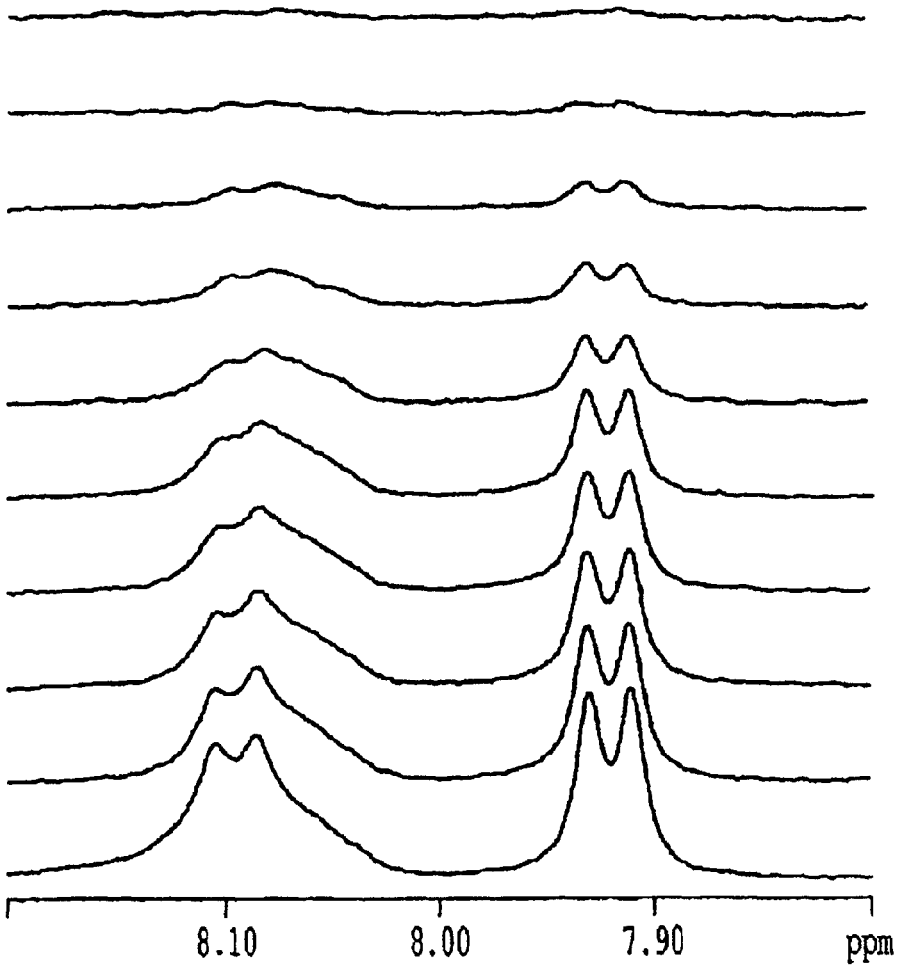
FIG. 2 shows stacked plots of $^{1}$H-NMR spectra, showing time-dependent decay of amide NH resonances for Trp (8.10 ppm) and D-Cha (7.90 ppm) residues of 7 in $d_6$-DMSO containing $D_2O$ after 10 minutes (bottom plot) and then 25, 40, 55, 70, 130, 190, 250, 385 and 520 minutes.

The 1D $^1$H-NMR spectrum of peptide 7 in $d_6$-DMSO at 24° C. shows 4 distinct resonances for amide-NH protons, as summarized in Table 3. To establish their possible involvement in intramolecular hydrogen bonds, a deuterium exchange experiment was performed by adding a 10-fold excess of $D_2O$ to the solution. Two of the amide-NH doublets disappeared immediately, along with resonances attributable to the N-terminal methylamine protons. However, the other two amide NH resonances, as well as a broad resonance at approximately 8.05 ppm, persisted for up to 6.5 hours (FIG. 2). These three slowly-exchanging protons are assigned to the amide NHs of Trp and d-Cha and the side chain amine of Lys, the slow exchange behaviour being characteristic of hydrogen-bonding. The amine assignment was established from the TOCSY spectrum where cross peaks were observed between the protonated amine and the ε, δ and γ $CH_2$ protons. A temperature dependence study (20–60° C.) of the amide-NH chemical shifts (Δδ/T=2.5 ppb/deg, dCha-NH; 6 ppb/deg, Trp-NH; 6.5 ppb, Lys-NH; 8.7 ppb, Arg-NH) unambiguously confirmed the involvement of the dCha-NH only in intramolecular hydrogen bonding.

TABLE 3

$^1$H-NMR Assignments[a] for 7 in $d_6$-DMSO

| Residue | [b]HN | Hα | Hβ | Hγ | Others |
|---|---|---|---|---|---|
| MePhe | — | 4.06 | 3.09, 3.06 | — | [c]7.17, 7.29; [d]2.46; [f]8.98 |
| Lys | 8.83 | 4.54 | 1.74, 1.55 | 1.32 | [e]1.51; [f]2.74, [g]7.76 ($NH_2$) |
| Pro | — | 4.30 | 2.084, 1.74 | 1.88, 1.78 | [e]3.61, [f]3.48 |
| d-Cha | 7.91 | 4.35 | 1.19, 1.06 | 0.76 | [e]1.43, 1.08; [f]1.61, 1.58; 0.73 |
| Trp | 8.01 | 4.65 | 3.11, 2.94 | — | [c]6.97, 7.06, 7.13, 7.32, 7.65; [g]10.80 |

TABLE 3-continued

| $^1$H-NMR Assignments[a] for 7 in $d_6$-DMSO | | | | | |
|---|---|---|---|---|---|
| Residue | [b]HN | Hα | Hβ | Hγ | Others |
| d-Arg | 8.44 | 4.20 | 1.73, 1.58 | 1.42 | [e]3.08; [g]7.60 |

[a]Referenced to residual $d_6$-DMSO at 2.50 ppm.
[b]Amide NHS, $^3$'NH-CaH values (Hz): 7.91 (Lys), 7.77 (d-Arg), 8.34 (Trp), 8.53 (d-Cha).
[c]Aromatics
[d]N-Me.
[e]Hδ.
[f]Hϵ
[g]NH/$NH_2$ amine.

Figure 3:
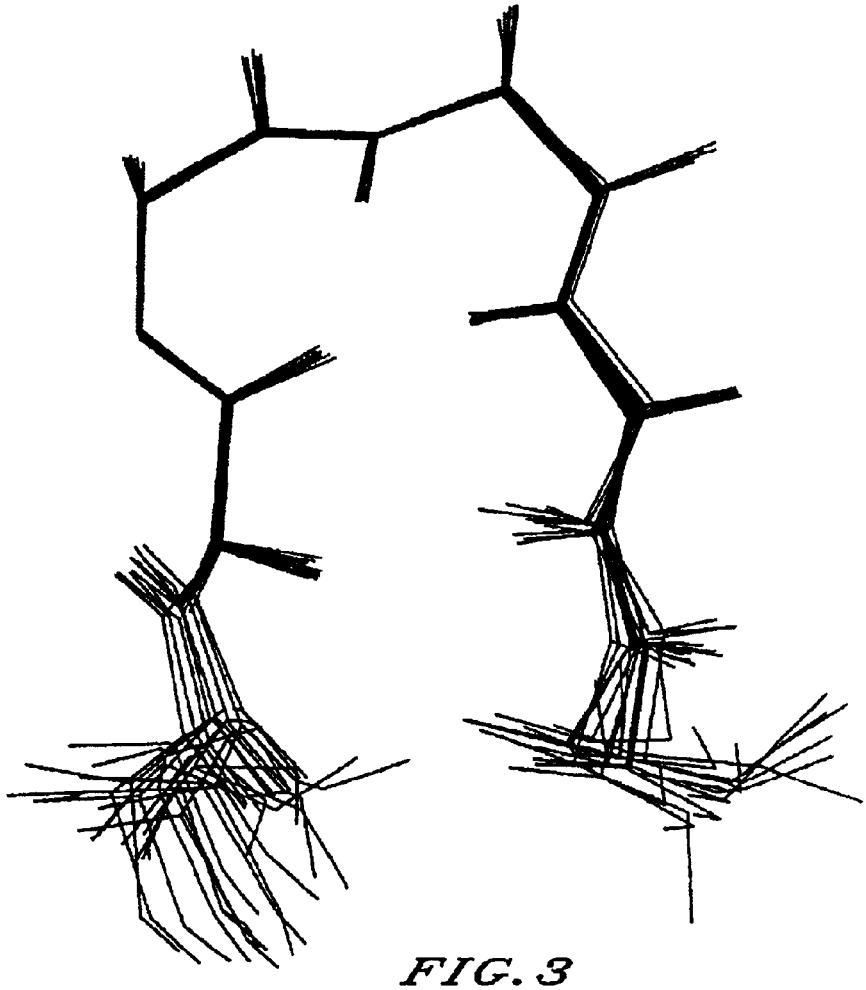
FIG. 3 shows backbone C, N, O atoms of twenty lowest energy minimized NMR structures of 7 in $d_6$-DMSO at 24° C.)

A series of 2D $^1$H-NMR spectra were measured for 7 at 24° C. in $d_6$-DMSO to determine the three-dimensional structure. TOCSY and DFQ-COSY experiments were used to identify residue types, while sequential assignments were made from analysis of NOESY data. From a series of 100 structures generated from NOESY data, fifty of the lowest energy structures were subjected to restrained molecular dynamics (200K–500K) and energy minimised. A set of 20 calculated structures with a root mean square deviation (rmsd)<0.5 Å (backbone atoms) are superimposed in FIG. 3, and clearly depict a turn conformation.

Figure 4:
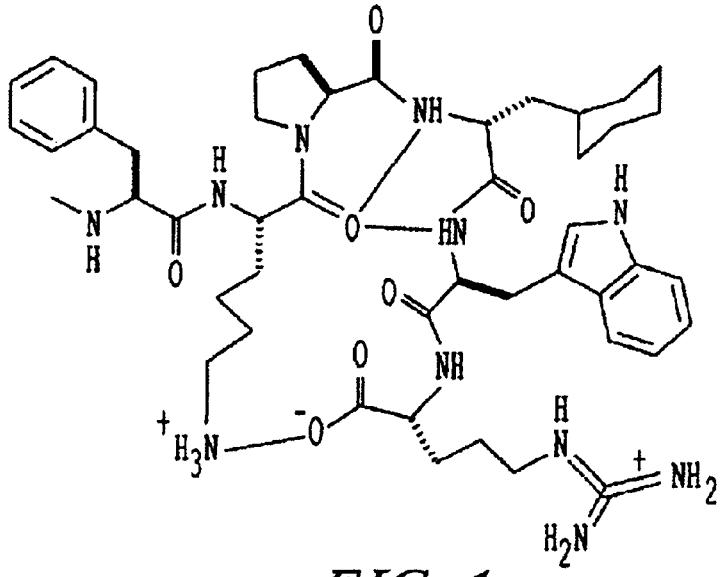
FIG. 4 shows a schematic representation of H-bonding in the structure of 7 from proton NMR spectra in $d_6$-DMSO.

In combination, the NMR constraint data, $^3$NH-CαH values, deuterium exchange and temperature dependence data establish an unusual turn structure for hexapeptide 7 which is constrained by up to three hydrogen bond, as shown in FIG. 4. The evidence is very strong for one intramolecular hydrogen bond from dCha-NH . . . OC-Lys (2.72 Å, N—H . . . O angle 157°, C═O . . . H angle 84°), forming a 7-membered ring that defines an inverse γ-turn. The dChaNH—O-TrpNH angle is 56.4°. The deuterium exchange data and NMR constraint data together point to a second intramolecular hydrogen bond Trp-NH . . . OC-Lys (3.31 Å, N—H . . . O angle 159°, CO . . . H angle 137.3°) forming a 10-membered ring characteristic of a β-turn. The ϕ and ψ angles (100 $_2$=−58.4°, $\psi_2$=62.0°; ϕ=96.6°, $\psi_3$=16.6°) most closely match a type II β-turn (Bandekar, 1993; Hutchinson and Thornton, 1994) which is distorted by the presence of the γ-turn wholly within the β-turn.

To our knowledge this is the first example of an intramolecular hydrogen bond between residues within a β-turn, although there are many examples of hydrogen bonds between a residue within the "10 membered ring" of a β-turn and a residue outside of it (Bandekar, 1993). A third hydrogen bond (2.76 Å, N—H . . . O angle 160.3°), between the side-chain amine of Lys and the C-terminal carboxylate, is suggested by the NMR constraint data, by slow NH/ND exchange and by detection of a weak NOE between Lys-NH . . . Trp-α$CH_2$. This may further constrain the molecule into the observed turn conformation. Such ion-pairing is common in dipolar aprotic solvents such as dimethylsulphoxide and may also be relevant in a hydrophobic protein environment.

NMR solution structures have also been determined for several of the cyclic antagonists described in the following examples, and show that in each case the type II β-turn is preserved and stabilized by the cyclic structure.

The constraining β and γ turns proposed in the linear peptide 7 have parallels in cyclic peptides. We have previously detected overlapping β and γ turns in a cyclic octapeptide from ascidiacyclamide (Abbenante et al, 1996). Combinations of a β- and γ-turn have also been found in the backbones of cyclic penta- and hexapeptides, particularly those containing alternating D- and L-amino acids (Marraud and Aubry 1996; Fairlie et al, 1995; Kessler et al, 1995; Stradley et al, 1990). For example a type II β-turn and an inverse γ-turn have been identified in cyclic antagonists c-(D-Glu-Ala-D-allo-Ile-Leu-D-Trp] (Ihara et al, 1991; Coles et al, 1993; Ihara et al, 1992; Bean et al, 1994) and c-(D-Asp-Pro-D-Val-Leu-D-Trp) (Bean et al, 1994) for endothelin receptors, and in members of the rhodopsin family of G protein-coupled receptors with seven transmembrane domains (X. -M. Cheng et al, 1994). In the latter case, as in 7, an inverse γ-turn forms between residues (Asp-CO . . . Val-NH, Lys-CO . . . dCha-NH) that flank the proline.

EXAMPLE 3

Structure-Activity Relationships in Vitro

Figure 5A:
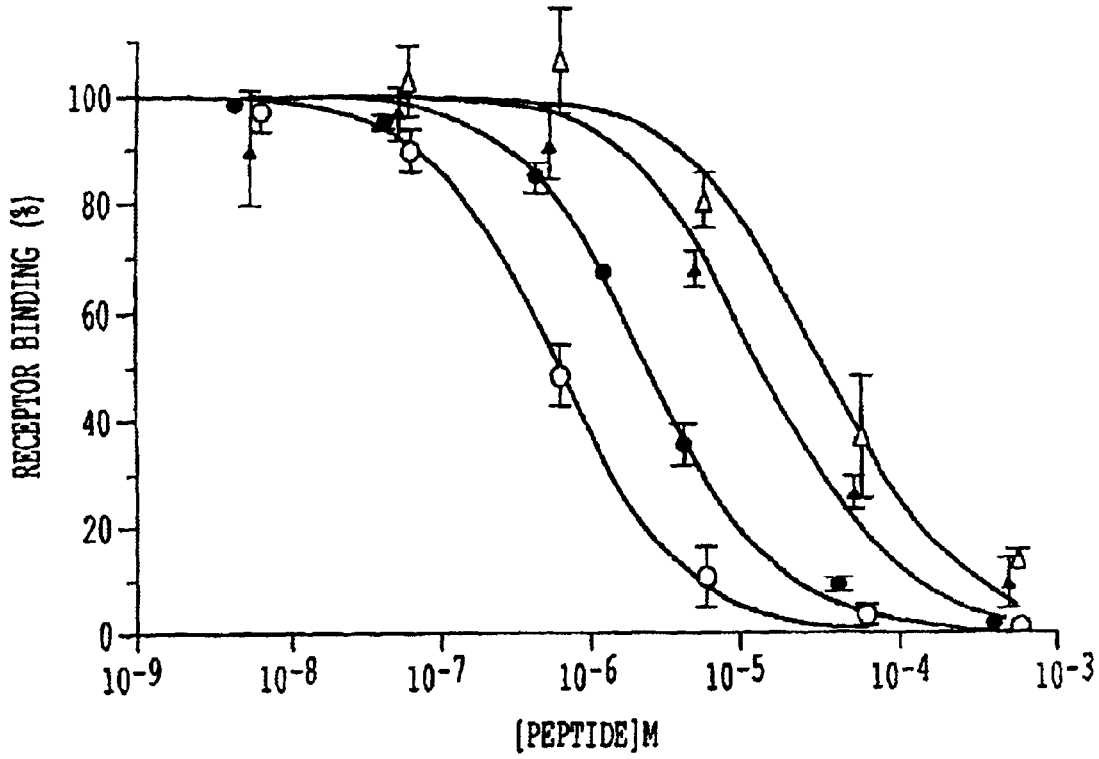
FIG. 5a shows (a) receptor binding, as indicated by inhibition of binding of $^{125}$I-C5a to human PMNs by 7 (●); 8 (Δ); 9 (▲); 12 (○)

We also examined the receptor-binding and antagonist activity of the hexapeptide 7 for comparison with our compounds. The previous-report by Konteatis et al (1994) concerned the ability of 7 to compete with C5a binding to receptors on isolated PMN membranes ($IC_{50}$ 70 nM), which is not necessarily physiologically relevant. We examined competition between 7 and C5a using intact PMN cells, and found that, under these conditions, 7 binds with much lower receptor affinity of $IC_{50}$ 1.8 μM. We confirmed that 7 is a full antagonist with no agonist properties. These results are summarized in FIG. 5a and Table 4. The relative affinity (ratio) of 7 for the C5aR in intact PMNs in our assays was similar to that previously reported for isolated PMN membranes.

Figure 5B:
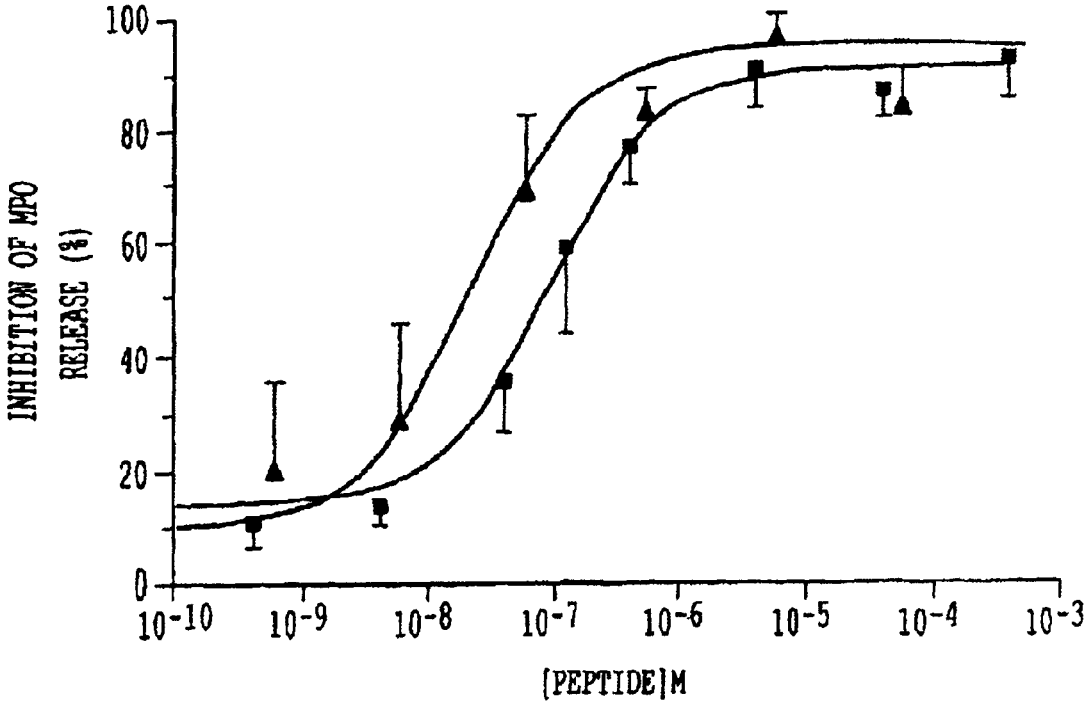
FIG. 5b shows C5a antagonist potency as inhibition of myeloperoxidase (MPO) release from human PMNs by: 7 (■, n=9) and 12 (▲, n=4).

We have also found that 7 shows antagonist activity against both C5a (FIG. 5b) and a C-terminal agonist decapeptide analogue 4 (YSFKPMPLaR) (Finch et al, 1997) of the C-terminus $C5a_{65-74}$, suggesting that it acts on site 2 of the receptor. Compounds 7 and 4 have similar μM affinity for the receptor C5aR on intact polymorphonuclear leukocytes, as shown in Table 4.

A new discovery from the data in Table 4 is the linear correlation between the log of binding affinities and the log of antagonist potencies for these Site 2 antagonists (compounds 7–12, Table 4). The importance of this linear relationship is that since receptor affinity and antagonist activity are directly proportional, the experimentally simpler approach of measuring receptor binding may be used to estimate the antagonist activity for such small compounds, provided that there is no evidence of agonist activity.

TABLE 4

| Receptor-Binding Affinities[a] and Antagonist Activities[b] in Human PMNs | | | | |
|---|---|---|---|---|
| | Compound | Receptor Affinity[a] $IC_{50}$ (μM) | Antagonist Potency[b] $IC_{50}$ (μM) | Agonist Activity[c] |
| SEQ. ID NO: 7 | MeFKP (dCha) Wr | 1.8 (15) | 0.085 (9) | No |
| SEQ. ID NO: 8 | MeFKP (dCha) Wr-$CONH_2$ | 14 (5) | 0.5 (3) | No |

TABLE 4-continued

Receptor-Binding Affinities[a] and Antagonist Activities[b] in Human PMNs

| | Compound | Receptor Affinity[a] $IC_{50}$ (μM) | Antagonist Potency[b] $IC_{50}$ (μM) | Agonist Activity[c] |
|---|---|---|---|---|
| SEQ. ID NO: 9 | MeFKP (dCha) WR | 11 (5) | 0.7 (3) | No |
| SEQ. ID NO: 10 | MeFKPLWR | 144 (1) | >1000 (3) | nd |
| SEQ. ID NO: 11 | Ac-F-[KP (dCha) Wr | 3.2 (40) | 0.090 (5) | No |
| SEQ. ID NO: 12 | Ac-F-[OP (dCha) Wr | 0.28 (6) | 0.012 (4) | No |
| SEQ. ID NO: 4 | YSFKPMPLaR | 6.0[d] | — | Yes |
| SEQ. ID NO: 1 | $C5a_{65-74}$, ISHKDMQLGR | >1000[e] | — | — |
| | C5a | 0.0008 (9) | — | Yes |

Number of experiments in parenthesis. Corrected for amino acid content
Square brackets indicate cyclic portion.
nd = not determined
[a]50% reduction in binding of $^{125}$I-C5a to intact human PMNs
[b]50% reduction in myeloperoxidase secretion from human PMNs mediated by 100 nM C5a
[c]Agonist activity in dose range 0.1 nM-1 nM
[d]Finch et al, 1997;
[e]Kawai et al, 1991

It has previously been proposed that the C-terminus of C5a and of agonist peptides is essential for activity, due to its interaction with a positively-charged Arg206 of the receptor (DeMartino et al, 1995). We confirm here that the C-terminal carboxylate is indeed important for activity (8 vs. 7), but wondered whether the origin of this effect might be due to hydrogen bonding between the carboxylate anion and the positively charged amine side chain of Lys. Conversion to the amide (8) certainly reduces both receptor-affinity and antagonist activity approximately 5-fold. Changing chirality of the Arg-Cα (9 vs. 7) causes a similar reduction in activity, and replacing dCha with the less bulky Leu residue (10) is also detrimental to receptor binding. However, potency is recovered for cyclic compounds 11 and 12, in which an amide bond is tolerated at the C-terminus, consistent with the structural interpretation above that the advantage of the carboxylate in 7 may be associated with intramolecular hydrogen bonding. The replacement of this hydrogen bond it 7 with a covalent amide bond in 11 and 12 more effectively stabilizes the turn conformation.

FIG. 5C compares C5aR binding and antagonist potency in vitro on human PMNs for compounds 15 and 17 with those for compound 7. Both 15 and 17 are potent inhibitors at nM concentrations of the action of C5a and the binding of $^{125I\text{-}C}$5a to its receptor (e.g. 4, Kb=1.4 nM). Their cyclic nature and the acetylation at the N-terminal phenylalanine both protect against the proteolytic degradation typically encountered by peptides, making such cyclic compounds more suitable than acyclic peptides as drug candidates. The results are shown in Table 5.

TABLE 5

Receptor Binding and Antagonist Activity of Cyclic Molecules

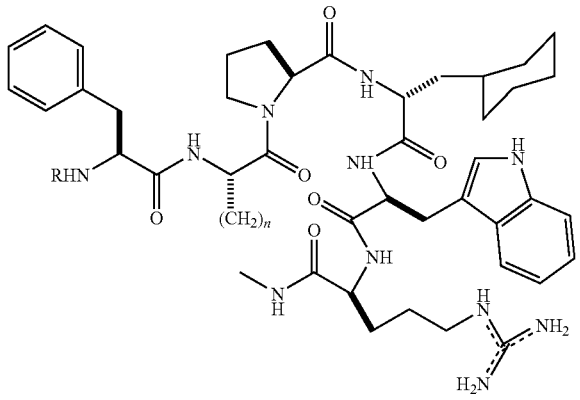

| Compound | n | R | Isomer* | Receptor Affinity μM | Agonist Activity |
|---|---|---|---|---|---|
| SEQ. ID NO: 13 | 1 | H | S- | 9 | No |
| SEQ. ID NO: 14 | | | R- | 34 | No |
| SEQ. ID NO: 15 | 2 | H | S- | 0.3 | No |
| SEQ. ID NO: 16 | | | R- | 3.7 | No |
| SEQ. ID NO: 17 | 3 | Ac | S- | 0.3 | No |
| SEQ. ID NO: 11 | | Ac | R- | 38 | No |
| SEQ. ID NO: 18 | 4 | Ac | S- | 3.2 | No |
| SEQ. ID NO: 12 | | Ac | R- | 51 | No |

Refers to stereochemistry of Arg side chain

EXAMPLE 4

Cyclic Antagonists of C5a

Some examples of these cyclic antagonists and their apparent receptor-binding affinities and antagonist potencies are given in Tables 4, 5 and 6 as well as in FIGS. 5 and 6. In the tables the single letter code for amino acids is used.

TABLE 6

| | PEPTIDE | $pD_2 \pm SE^a$ | $IC_{50}$ (M)$^a$ | (n) | $pD_2 \pm SE^b$ | $IC_{50}$ (M)$^b$ | (n) |
|---|---|---|---|---|---|---|---|
| Effect of Cyclisation on Antagonist Binding Affinity and Antagonist Potency | | | | | | | |
| SEQ. ID NO: 11 | AcF-[KPdChaWr] | 5.49 ± 0.22 | 3.2 | 4 | 7.07 ± 0.29 | 0.09 | 5 |
| SEQ. ID NO: 12 | AcF-[OPdChaWr] | 6.44 ± 0.14* | 0.4 | 9 | 7.30 ± 0.09 | 0.05 | 9 |
| SEQ. ID NO: 19 | [FWPdChaWr] | 4.37 ± 0.36* | 43 | 3 | nd | | |
| SEQ. ID NO: 20 | AcF-[KMdChaWr] | 4.81 ± 0.06 | 15 | 2 | nd | | |
| SEQ. ID NO: 21 | AcF-[KKdChaWr] | 3.94 ± 0.4 | 116 | 3 | 4.88 | 13 | 1 |
| Effect of length of linker in cycle on antagonist binding affinity and antagonist potency | | | | | | | |
| SEQ. ID NO: 22 | AcF-[XPdChaWr] | 5.02 ± 0.07 | 9.5 | 3 | 4.71 ± 0.23 | 20 | 3 |
| SEQ. ID NO: 23 | AcF-[$X^2$PdChaWr] | 4.77 ± 0.14* | 17 | 3 | 6.09 ± 0.08* | 0.8 | 3 |
| SEQ. ID NO: 12 | AcF-[OPdChaWr] | 4.60 ± 0.06* | 16 | 4 | 6.42 ± 0.10 | 0.4 | 4 |
| SEQ. ID NO: 24 | AcKF-[OPdChaWr] | 4.96 ± 0.03 | 11 | 3 | 6.73 | 0.2 | 1 |
| SEQ. ID NO: 14 | F-[XPdChaWr] | 4.39 ± 0.10* | 41 | 3 | nd | | |
| SEQ. ID NO: 16 | F-[$X^2$PdChaWr] | 5.42 ± 0.05 | 3.8 | 3 | 6.70 ± 0.04 | 0.4 | 3 |
| SEQ. ID NO: 25 | F-[OPdChaWr] | 5.51 ± 0.07 | 3.1 | 3 | 5.79 ± 0.34* | 1.6 | 3 |
| SEQ. ID NO: 26 | F-[KPdChaWr] | 5.09 ± 0.08 | 8.1 | 3 | 5.55 ± 0.57* | 2.8 | 3 |
| Effect of L-Arg on antagonist binding affinity and antagonist potency | | | | | | | |
| SEQ. ID NO: 17 | AcF-[OPdChaWr] | 6.57 ± 0.05 | 0.3 | 3 | 7.91 ± 0.17* | 0.01 | 3 |
| SEQ. ID NO: 13 | F-[XPdChaWr] | 4.98 ± 0.05 | 10 | 3 | 5.63 ± 0.13* | 2.4 | 3 |
| SEQ. ID NO: 15 | F-[$X^2$PdChaWr] | 6.50 ± 0.04* | 0.3 | 5 | 7.36 ± 0.13 | 0.04 | 3 |
| SEQ. ID NO: 27 | F-[OPdChaWr] | 7.21 ± 0.01* | 0.06 | 3 | 7.41 ± 0.14 | 0.04 | 3 |
| SEQ. ID NO: 28 | F-[KPdChaWr] | 6.50 ± 0.12* | 0.3 | 4 | 6.69 ± 0.04 | 0.2 | 3 |

These results demonstrate:

(1) that the cyclic molecules have higher apparent receptor affinity and may be more potent antagonists than acyclic (linear) peptides, (2) that one of the two possible cyclic diastereomers is consistently favoured for binding to the C5a receptor, and it is surprisingly the opposite stereochemistry (L-arginine) to that favoured in the linear compounds (D-arginine)

(3) that the cycles have an optimum ring size for receptor-binding, (4) that there is a pseudo-linear relationship between log (antagonist potency) and log (receptor affinity).

Tables 5 and 6 list the C5a receptor affinities of some examples of cyclic antagonists of C5a, and their ability to bind to, and inhibit, binding of C5a to human PMNs is illustrated in FIG. 6. Surprisingly these data show that the L-arginine is preferred over the D-arginine, in contrast to the linear compound 7 in which the D-arginine confers higher affinity for the receptor than does L-arginine. The data also show that the size of the macrocycle is optimal when n=2 or 3, the smaller cycle where n=1 and the larger cycle when n=4 being clearly less active. This requirement for a tightly constrained cycle is probably due to the need to correctly position the attached side chain residues of, for example, Trp, dCha, Arg and Phe for interaction with the receptor.

EXAMPLE 5

Computer Modelling of Antagonist Structures

FIG. 7 compares the computer-modelled structure of the cyclic antagonist 12 with the NMR solution structure for the acyclic antagonist 7. These backbone structures are strikingly similar, and strongly suggest that the receptor-binding conformations of these molecules involve the same turn structure. Compound 12, a more potent antagonist than 11, also has a shorter linker, which tightens the turn and slightly alters the conformational space accessible to the key side chains of Phe, dCha, Trp and Arg. The conformational limitations placed on the hexapeptide derivative 12 by the cycle are responsible for a $\geqq 10^4$ increase in receptor-binding affinity over the conformationally flexible decapeptide C-terminus of C5a (1, Table 2).

There is a correlation between binding affinities and antagonist potency for the site 2 antagonists (compounds 7–12, Table 2). It thus appears that antagonist potency is dependent upon changes that occur at site 2 alone. Without wishing to be bound by any proposed mechanism, we believe that this may be because the mechanism of antagonism is related to conformational change to a turn conformation induced by 7 at site 2 of the receptor.

EXAMPLE 6

Characterisation of C5aRS on Different Cells

Currently there is no information about different types of C5aRs. We have previously shown marked differences in the responsiveness of different cells containing functional C5aRs to agonists (Sanderson et al, 1994, 1995; Finch et al, 1997) and we can now provide more information by examining potency and efficacy of selective agonists and antagonists relative to human recombinant C5a. For agonists, the tissue or cell selectivity may reveal functionally different receptors. Binding assays using human PMNs, U937 cells, or circulating monocytes are used to determine affinities for C5aRs. Selectivity for different C5aRs is ascertained by differential antagonism. This combined approach allows pharmacological characterisation of new agonists or antagonists, and may lead to a potential functional classification of C5aRson different cells.

EXAMPLE 7(a)

Neutropenia and C5a Antagonism In Vivo

Compounds were evaluated in an acute model of C5a-induced neutropenia. Transient neutropenia maximises 5 min after i.v. C5a and is profound, with >90% of circulating neutrophils disappearing from circulation at effective doses of C5a, as shown in FIG. 8. The neutropenia is due to transient adherence of circulating neutrophils to the vascular endothelium. Preliminary data show that neutropenia caused by i.v. C5a is blocked by a C5a antagonist. For example, F-[OPdChaWR], (1 mg/kg), given prior to 2 μg C5a i.v., inhibits C5a-induced neutropenia in vivo (FIG. 8)

EXAMPLE 7(b)

Inhibition of Lipopolysaccharide-Induced Effects by C5a Antagonists

LPS causes rapid neutropenia in rats. If this effect of LPS is blocked by C5a antagonists, then C5a may be of major importance in the acute effects of LPS, and the results shown in FIG. 9 were in agreement with this hypothesis. C5a antagonists were injected (bolus i.v.) 10 min prior to challenge with LPS. Rats were anaesthetised, and blood samples (0.3 ml) were taken for measurements of PMNs. PMNs are isolated and quantified. Preliminary results show that F-[OPdChaWR], (1 mg/kg), given prior to i.v. LPS, inhibits neutropenia.

The results also indicate that the C5a antagonist inhibits the increase in haematocrit caused by LPS, showing that vascular leakage of serum caused by LPS is also inhibited.

These results demonstrate that C5a receptor antagonists, such as those described in this invention, may have therapeutic utility in septicaemic individuals. The ability to inhibit the adherence of PMNs to vascular endothelium, and to inhibit the vascular leakage to LPS as shown by the reduction of haematocrit values, indicates powerful anti-inflammatory effects of these compounds against proinflammatory stimuli activating the complement system, such as endotoxin or LPS.

EXAMPLE 8

In Vivo Activity of Cyclic C5a Antagonists

Preliminary experiments in rats have revealed that the cyclic antagonists summarized in Table 5 are active at less than 20 mg/kg as anti-inflammatory agents in suppressing the onset of either carrageenan-induced paw oedema or adjuvant-induced polyarthritis. The maximally effective dosages for even moderately-effective antagonists are 10 mg/kg or less, given i.p. or p.o. Many anti-inflammatory drugs currently used in humans were initially evaluated in such assays, and also showed activity in these rat models of inflammation. These preliminary indications of efficacy in vivo indicate that C5a antagonists have therapeutic potential in human inflammatory conditions.

Using the rat carrageenan paw oedema assay, we found that a compound, AcF-[O—P-dCha-W-r], which is 100 times less active than 17 in vitro as a C5a antagonist in PMNs, has some in vivo activity in rats given 1 mg/kg of the compound I.P, 30 min prior to the carageenan injection. Paw swelling was measured for up to 4.5 hr. The results, shown in FIG. 10, suggest that even this weak C5a antagonist significantly inhibits development of the oedema after 180 and 270 min. This anti-inflammatory activity suggests that C5a receptor antagonists, such as those described in this invention, may have therapeutic activity in diseases involving vascular leakage following inflammatory stimuli.

In recent years there have been many attempts to mimic β- and γ-turn peptides that represent bioactive protein surfaces, resulting in notable mimetics for RGD (arginine-glycine-aspartate) peptides, somatostatin and opioid peptides, to name a few derived through structure-activity relationships (see for example Marraud and Aubry, 1996; Fairlie et al, 1995). Most of these examples preserve a turn structure through cyclisation of the peptide. On the other hand, there are comparatively few short acyclic peptides that have been found to have substantial turn structure in solution (Dyson et al, 1988; Rizo and Gierasch, 1992; Pracheur et al, 1994). It is usually argued that short acyclic peptides adopt a myriad of solution structures that may include small populations of turn structures that are responsible for bioactivity.

This invention describes a series of conformationally-constrained turn-containing molecules that are preorganized for binding to the same G protein-coupled receptor(s) of human cells that are targeted by human C5a. The invention is applicable to other C protein-coupled receptors.

The principal feature of the compounds of the invention is the preorganized arrangement, which brings at least three hydrophobic groups and a charged group into neighbouring space, creating a hydrophobic surface 'patch'. These results enable the design and development of even more potent conformationally-constrained, small molecule antagonists of C5a.

In the light of the aforementioned prior art, it was surprising to find that a C-terminal carboxylate was not necessary in our compounds in order to obtain good receptor-binding or antagonist activity. The cyclic antagonists have an amide bond at the 'C-terminal' arginine position. The replacement of the carboxylate in 7 with a covalent amide bond effectively stabilises the required turn conformation.

Cyclic and non-peptidic antagonists have several important advantages over peptides as drugs. The cycles described in this invention are stable to proteolytic degradation for at least several hours at 37° C. in human blood or plasma, or in human or rat gastric juices or in the presence of digestive enzymes such as pepsin, trypsin and chymotrypsin. In contrast, short peptides composed of L-amino acids are rapidly degraded to their component amino acids within a few minutes under these conditions. A second advantage lies in the constrained single conformations adopted by the cyclic and non-peptidic molecules, whereas acyclic or linear peptides are flexible enough to adopt several structures in solution other than the required receptor-binding structure. Thirdly, cyclic and non-peptidic compounds such as those described in this invention are usually more lipid-soluble and more pharmacologically bioavailable as drugs than peptides, which can rarely be administered orally. Fourthly, the plasma half-lives of cyclic and non-peptidic molecules are usually longer than those of peptides.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Abbenante, G., Fairlie, D. P., Gahan, L. R., Hanson, G. R., Pierens, G. K. and van den Brenk, A. L. J. Am. Chem. Soc., 1996 118 10384–10388

Bandekar, J. Vib. Spectros., 1993 5 143–173

Bean, J. W., Peishoff, C. E. and Kopple, K. D. Int. J. Protein Res., 1994 44 223

Cheng, X. M., Doherty, A. M., Nikam, S. S. Curr. Med. Chem. 1994 1 271–312

Coles, M., Sowemimo, V., Scanlon, D., Munro, S. L. A., Craik, D. J. J. Med. Chem., 1993 36 2658

DeMartino, J. A., Konteatis, Z. D., Siciliano, S. J., Van Riper, G., Underwood, D. J., Fischer, P. A., Springer, M. S. J. Biol. Chem., 1995 270 15966–15969

DeMartino, J. A., Van Riper, G., Siciliano, S. J., Molineaux, C. J., Konteatis, Z. D., Rosen, H. Springer, M. S. J. Biol. Chem., 1994 269 14446–14450.

Drapeau, G., Brochu, S., Godin, D., Levesque, L., Rioux, F. and Marceau, F. Biochem. Pharm., 1993 45 1289–1299

Dyson, H. J., Rance, M., Hougten, R. A., Lerner, R. A. and Wright, P. E. J. Mol. Biol., 1988 201 161–200

Ember, J. A., Sanderson, S. D., Taylor, S. M., Kawahara, M. and Hugli, T. E. J. Immunol., 1992 148 3165–3173

Fairlie, D. P., Abbenante, G. and March, D. Curr. Med. Chem., 1995 2 672–705

Fairlie, D. P., Whitehouse, M. and Broomhead, J. Chem. Biol. Interact., 1987 61 277–291

Finch, A. M., Vogen, S. M., Sherman, S. A., Kirnarsky, L., Taylor, S. M., and Sanderson, S. D. J. Med Chem., 1997 40 877

Gerard, N and Gerard, C. Nature, 1991 349 614–617

Gerard, C and Gerard, N. P. Am. Rev. Immunol., 1994 12 775–808

Haviland, D. L., McCoy, R. L., Whitehead, W. T., Akama, H., Molmenti, E. P., Brown, A., Haviland, J. C., Parks, W. C., Perlmutter, D. H. and Wetsel, R. A. J. Immunol., 1995 154 1861–1869

Hutchinson, E. G. and Thornton, J. M., Protein Sci., 1994 3 2207–2216

Ihara, M., Fukuroda, T., Saeki, T., Nishikibe, M., Kojiri, K., Suda, H. and Yano, M. Biochem. Biophys. Res. Comm., 1991 178 132–137

Ihara, M., Noguchi, K., Sacki, T., Fukuroda, T., Tsuchida, S., Kimura, S., Fukami, T., Ishikawa, K., Nishikibe, M., and Yano, M. Life Sciences, 1992 50 247

Kawai, M., Quincy, D. A., Lane, B., Mollison, K. W., Luly, J. R., Carter, G. W. J. Med. Chem., 1991 34 2068–71

Kawai, M., Quincy, D. A., Lane, B., Mollison, K. W., Or, Y. -S., Luly, J. R., and Carter, G. W. J. Med. Chem., 1992 35 220–223

Kessler, H., Diefenbach, B., Finsinger, D., Geyer, A., Gurrath, M., Goodman, S. L., Hoelzemann, G., Haubner, R., Jonczyk, A. et al Lett. Pept. Sci., 1995 2 155–160

Kohl, J., Lubbers, B. Klos, A., et al. Eur. J. Immunol., 1993 23 646–652

Konteatis, Z. D., Siciliano, S. J., Van Riper, G., Molineaux, C. J., Pandys, S., Fischer, P., Rosen, H., Mumford, R. A., and Springer, M. S. J. Immunol., 1994 153 4200–4204

Marraud, M. and Aubry, A. Biopolymers, 1996 40 45–83

Morgan, E. L., Sanderson, S. D., Scholz, W., Noonal, D. J., Weigle, W. O. and Hugli, T. E. J. Immunol., 1992 48 3937–3942

Pracheur, Bossus, M., Gras-Masse, H., Quiniou, E., Tartar, A. and Craescu, C. T. J. Biochem., 1994 220 415–425

Rizo, J. and Gierasch, L. M. Ann. Rev. Biochem., 1992 61 387

Sanderson, S. D., Ember, J. A., Kirnarsky, L., Sherman, S. A., Finch, A. M., Taylor, S. M. J. Med. Chem., 1994 37 3171–3180

Sanderson, S. D., Kirnarsky, L., Sherman, S. A., Vogen, S. M., Prakesh, O., Ember, J. A., Finch, A. M. and Taylor, S. M. J. Med. Chem., 1995 38 3669–3675

Siciliano, S. J., Rollins, T. E., DeMartino, J., Konteatis, Z. Malkowitz, L., VanRiper, G., Bondy, S., Rosen, H. and Springer, M. S. Proc. Nat. Acad. Sci. USA, 1994 91 1214–1218.

Slim, E. The Natural Immune System. Humoral Factors., 1993; IRL Press, Oxford University Press, Oxford.

Tempero, R. M., Hollingsworth, M. A., Burdick, M. D., Finch, A. M., Taylor S. M., Vogen, S. M., Morgan, E. L., and Sanderson, S. D. J. Immunol., 1997 158 1377–1382

Stradley, S., Rizo, J., Bruch, M., Stroup, A. and Gierasch, L. Biopolymers, 1990 29 263–287.

Walker W. R. and Whitehouse, M. W. Agents & Actions, 1978 8 85

Ward, J. R. and Cloud, R. S. J. Pharmacol. Exp. Ther., 1966 152 116

Whaley, K. Complement in Health and Disease. Immunology and Medicine Series, Ed., Reeves, W. G., 1987, MTP Press Ltd, Lancaster Whitehouse, M. W. Handbook of Animal Models for the Rheumatic Diseases, Eds. Greenwald, R. A., Diamond, H. S., Vol. 1, pp 3–16 CRC Press.

Winter, C. A. and Nuss, G. W. Arth. & Rheumatism, 1966 9 394

Zhang, X., Boyar, W., Galakatos, N. and Gonella, N. C. Protein Sci., 1997 6 65–72

Zuiderweg, E. R. P., Nettesheim, D. G., Molison, K. W., Carter, G. W. Biochemistry, 1989 28 172–185; 29 2895–2905.

SEQUENCE LISTING

```
<160> NUMBER OF SEQ ID NOS: 28

<210> SEQ ID NO 1
<211> LENGTH: 10
<212> TYPE: PRT
<213> ORGANISM: Artificial Sequence
<220> FEATURE:
<223> OTHER INFORMATION: synthetic peptide

<400> SEQUENCE: 1

Ile Ser His Lys Asp Met Gln Leu Gly Arg
1               5                   10


<210> SEQ ID NO 2
<211> LENGTH: 10
<212> TYPE: PRT
<213> ORGANISM: Artificial Sequence
<220> FEATURE:
<223> OTHER INFORMATION: synthetic peptide
```

<400> SEQUENCE: 2

Tyr Ser Phe Lys Asp Met Gln Leu Gly Arg
1 5 10

<210> SEQ ID NO 3
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (9)..(9)
<223> OTHER INFORMATION: Xaa is D-Ala

<400> SEQUENCE: 3

Tyr Ser Phe Lys Asp Met Pro Leu Xaa Arg
1 5 10

<210> SEQ ID NO 4
<211> LENGTH: 10
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (9)..(9)
<223> OTHER INFORMATION: Xaa is D-Ala

<400> SEQUENCE: 4

Tyr Ser Phe Lys Pro Met Pro Leu Xaa Arg
1 5 10

<210> SEQ ID NO 5
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (11)..(11)
<223> OTHER INFORMATION: MOD_RES: Acp
<220> FEATURE:
<221> NAME/KEY: misc_feature
<222> LOCATION: (20)..(20)
<223> OTHER INFORMATION: Xaa is D-Ala

<400> SEQUENCE: 5

Arg Ala Ala Arg Ile Ser Leu Gly Pro Arg Xaa Tyr Ser Phe Lys Pro
1 5 10 15

Met Pro Leu Xaa Arg
20

<210> SEQ ID NO 6
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (10)..(10)
<223> OTHER INFORMATION: MOD_RES: Acp
<220> FEATURE:
<221> NAME/KEY: misc_feature
<222> LOCATION: (19)..(19)
<223> OTHER INFORMATION: Xaa is D-Ala -continued

<400> SEQUENCE: 6

Lys Tyr Lys His Ser Val Val Lys Lys Xaa Tyr Ser Phe Lys Pro Met
1 5 10 15

Pro Leu Xaa Arg
20

<210> SEQ ID NO 7
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: D-Arg

<400> SEQUENCE: 7

Phe Lys Pro Xaa Trp Arg
1 5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: MOD_RES
<222> LOCATION: (6)..(6)
<223> OTHER INFORMATION: residue is substituted with (CO)NH2
<220> FEATURE:
<221> NAME/KEY: misc_feature
<222> LOCATION: (6)..(6)
<223> OTHER INFORMATION: D-Arg

<400> SEQUENCE: 8

Phe Lys Pro Xaa Trp Arg
1 5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: METHYLATION
<220> FEATURE:
<221> NAME/KEY: misc_feature
<222> LOCATION: (4)..(4)
<223> OTHER INFORMATION: Xaa is D-cylcohexylalanine -continued

<400> SEQUENCE: 9

Phe Lys Pro Xaa Trp Arg
1 5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: METHYLATION

<400> SEQUENCE: 10

Phe Lys Pro Leu Trp Arg
1 5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cylcohexylalanine
<220> FEATURE:
<221> NAME/KEY: misc_feature
<222> LOCATION: (6)..(6)
<223> OTHER INFORMATION: D-Arg

<400> SEQUENCE: 11

Phe Lys Pro Xaa Trp Arg
1 5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Orn
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: D-cyclohexylalanine
<220> FEATURE:
<221> NAME/KEY: misc_feature
<222> LOCATION: (6)..(6)
<223> OTHER INFORMATION: D-Arg -continued

<400> SEQUENCE: 12

Phe Xaa Pro Xaa Trp Arg
1 5

<210> SEQ ID NO 13
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: SITE
<222> LOCATION: (1)..(2)
<223> OTHER INFORMATION: between residues 1 and 2: (CH2)-NH2
<220> FEATURE:
<221> NAME/KEY: SITE
<222> LOCATION: (1)..(5)
<223> OTHER INFORMATION: cyclic portion is from residue 5 and the
(CH2) NH2 moiety present between residues 1 and 2
<220> FEATURE:
<221> NAME/KEY: misc_feature
<222> LOCATION: (3)..(3)
<223> OTHER INFORMATION: Xaa is D-cyclohexylalanine

<400> SEQUENCE: 13

Phe Pro Xaa Trp Arg
1 5

<210> SEQ ID NO 14
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: between residues 1 and 2: (CH2)-NH2
<220> FEATURE:
<221> NAME/KEY: SITE
<222> LOCATION: (1)..(5)
<223> OTHER INFORMATION: cyclic portion is from residue 5 and the
(CH2)-NH2 moiety between residues 1 and 2
<220> FEATURE:
<221> NAME/KEY: misc_feature
<222> LOCATION: (3)..(3)
<223> OTHER INFORMATION: Xaa is D-cyclohexylalanine

<400> SEQUENCE: 14

Phe Pro Xaa Trp Arg
1 5

<210> SEQ ID NO 15
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: between residues 1 and 2: (CH2)2-NH2
<220> FEATURE:
<221> NAME/KEY: SITE
<222> LOCATION: (1)..(5)
<223> OTHER INFORMATION: cyclic portion is from residue 5 and the
(CH2)2-NH2 moiety between residues 1 and 2
<220> FEATURE:
<221> NAME/KEY: misc_feature
<222> LOCATION: (3)..(3)
<223> OTHER INFORMATION: Xaa is D-cyclohexylalanine

<400> SEQUENCE: 15

-continued

Phe Pro Xaa Trp Arg
1 5

<210> SEQ ID NO 16
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: between residues 1 and 2: (CH2)2-NH2
<220> FEATURE:
<221> NAME/KEY: SITE
<222> LOCATION: (1)..(5)
<223> OTHER INFORMATION: cyclic portion is from residue 5 and the
(CH2)2-NH2 moiety between residues 1 and 2
<220> FEATURE:
<221> NAME/KEY: misc_feature
<222> LOCATION: (3)..(3)
<223> OTHER INFORMATION: Xaa is D-cyclohexylalanine

<400> SEQUENCE: 16

Phe Pro Xaa Trp Arg
1 5

<210> SEQ ID NO 17
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Xaa is Orn
<220> FEATURE:
<221> NAME/KEY: misc_feature
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine

<400> SEQUENCE: 17

Phe Xaa Pro Xaa Trp Arg
1 5

<210> SEQ ID NO 18
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (2)..(2)
<223> OTHER INFORMATION: Orn
<220> FEATURE:
<221> NAME/KEY: SITE
<222> LOCATION: (2)..(6)
<223> OTHER INFORMATION: cyclic portion
<220> FEATURE:

-continued

<221> NAME/KEY: misc_feature
<222> LOCATION: (4)..(4)
<223> OTHER INFORMATION: Xaa is D-cyclohexylalanine

<400> SEQUENCE: 18

Phe Xaa Pro Xaa Trp Arg
1 5

<210> SEQ ID NO 19
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: SITE
<222> LOCATION: (1)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: D-Arg

<400> SEQUENCE: 19

Phe Trp Pro Xaa Trp Arg
1 5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: D-Arg

<400> SEQUENCE: 20

Phe Lys Met Xaa Trp Arg
1 5

<210> SEQ ID NO 21
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (2)..(6)
<223> OTHER INFORMATION: cyclic portion
<220> FEATURE:

-continued

<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: D-Arg

<400> SEQUENCE: 21

Phe Lys Lys Xaa Trp Arg
1 5

<210> SEQ ID NO 22
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (1)..(5)
<223> OTHER INFORMATION: cyclic portion is from residue 5 and the
(CH2)-NH2 moiety between residues 1 and 2
<220> FEATURE:
<221> NAME/KEY: SITE
<222> LOCATION: (2)..(2)
<223> OTHER INFORMATION: Xaa is (CH2)-NH2
<220> FEATURE:
<221> NAME/KEY: misc_feature
<222> LOCATION: (3)..(3)
<223> OTHER INFORMATION: Xaa is D-cyclohexylalanine
<220> FEATURE:
<221> NAME/KEY: misc_feature
<222> LOCATION: (5)..(5)
<223> OTHER INFORMATION: D-Arg

<400> SEQUENCE: 22

Phe Pro Xaa Trp Arg
1 5

<210> SEQ ID NO 23
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (1)..(2)
<223> OTHER INFORMATION: between residues 1 and 2: (CH2)-NH2
<220> FEATURE:
<221> NAME/KEY: SITE
<222> LOCATION: (1)..(5)
<223> OTHER INFORMATION: cyclic portion is from residue 5 and the
(CH2)2-NH2 moiety between residues 1 and 2
<220> FEATURE:
<221> NAME/KEY: misc_feature
<222> LOCATION: (3)..(3)
<223> OTHER INFORMATION: residue is D-cyclohexylalanine
<220> FEATURE:
<221> NAME/KEY: misc_feature -continued <222> LOCATION: (5)..(5)
<223> OTHER INFORMATION: D-Arg

<400> SEQUENCE: 23

Phe Pro Xaa Trp Arg
1 5

<210> SEQ ID NO 24
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: misc_feature
<222> LOCATION: (3)..(3)
<223> OTHER INFORMATION: Orn
<220> FEATURE:
<221> NAME/KEY: SITE
<222> LOCATION: (3)..(7)
<223> OTHER INFORMATION: cyclic portion
<220> FEATURE:
<221> NAME/KEY: misc_feature
<222> LOCATION: (5)..(5)
<223> OTHER INFORMATION: Xaa is D-cyclohexylalanine
<220> FEATURE:
<221> NAME/KEY: misc_feature
<222> LOCATION: (7)..(7)
<223> OTHER INFORMATION: D-Arg

<400> SEQUENCE: 24

Lys Phe Xaa Pro Xaa Trp Arg
1 5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Orn
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: D-cyclohexylalanine
<220> FEATURE:
<221> NAME/KEY: misc_feature
<222> LOCATION: (6)..(6)
<223> OTHER INFORMATION: D-Arg

<400> SEQUENCE: 25

Phe Xaa Pro Xaa Trp Arg
1 5

-continued

<210> SEQ ID NO 26
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: D-Arg

<400> SEQUENCE: 26

Phe Lys Pro Xaa Trp Arg
1 5

<210> SEQ ID NO 27
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa is Orn
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: L-Arg

<400> SEQUENCE: 27

Phe Xaa Pro Xaa Trp Arg
1 5

<210> SEQ ID NO 28
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: SITE
<222> LOCATION: (2)..(6)
<223> OTHER INFORMATION: cyclic portion
<220> FEATURE:
<221> NAME/KEY: misc_feature
<222> LOCATION: (4)..(4)
<223> OTHER INFORMATION: Xaa is D-cyclohexylalanine
<220> FEATURE:
<221> NAME/KEY: misc_feature
<222> LOCATION: (6)..(6)
<223> OTHER INFORMATION: L-Arg

<400> SEQUENCE: 28

Phe Lys Pro Xaa Trp Arg
1 5

What is claimed is:

1. A compound, which has antagonist activity against a C5a receptor, has no agonist activity against a C5a receptor, and has the general formula II:

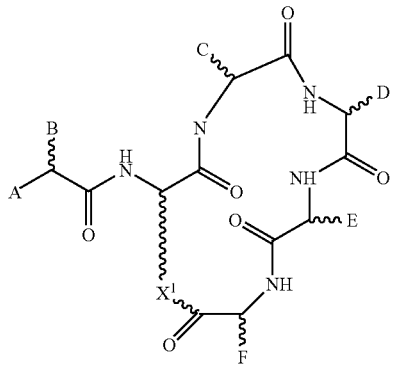

where A is H, alkyl, aryl, $NH_2$, NHalkyl, $N(alkyl)_2$, NHaryl or NHacyl;

B is an alkyl, aryl, phenyl, benzyl, naphthyl or indole group, or the side chain of a D- or L-amino acid selected from the group consisting of phenylalanine, homophenylalanine, tryptophan, homotryptophan, tyrosine, and homotyrosine;

C is the side chain of D-, L- or homo-amino acid selected from the group consisting of proline, alanine, leucine valine, isoleucine, arginine, histidine, aspartate, glutamate, glutamine, asparagine, lysine, tyrosine, phenylalanine, cyclohexylalanine, norleucine, tryptophan, cysteine and methionine;

D is the side chain of a D- or L-amino acid selected from the group consisting of cyclohexylalanine, homocyclohexylalanine, leucine, norleucine, homoleucine, homonorleucine and tryptophan;

E is the side chain of a D- or L-amino acid selected from the group consisting of tryptophan and homotryptophan;

F is the side chain of a D- or L-amino acid selected from the group consisting of arginine, homoarginine, lysine and homolysine or is one of the following side-chains

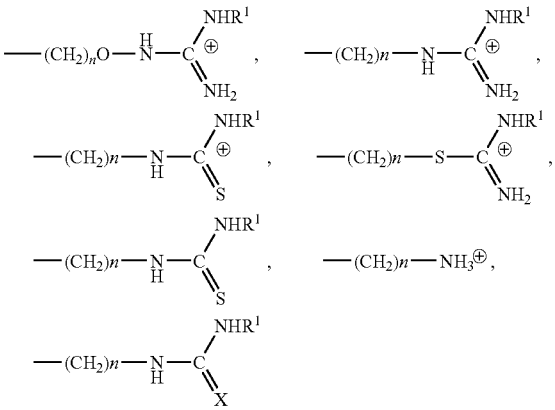

or another mimetic of an arginine side chain, where

X is NCN, $NNO_2$, $CHNO_2$ or $NSO_2NH_2$;

n is an integer from 1 to 4, and $R^1$ is H or an alkyl, aryl, CN, $NH_2$, OH, —CO—$CH_2CH_3$, —CO—$CH_3$, —CO—$CH_2CH_2CH_3$, —CO—$CH_2Ph$, or —CO-Ph; and $X^1$ is —$(CH_2)_n$NH— or $(CH_2)_n$—S—, —$(CH_2)_2$O—, —$(CH_2)_3$O—, —$(CH_2)_3$—, —$(CH_2)_4$—, or —$CH_2$COCHRNH—, where R is the side chain of any common or uncommon amino acid, and where n is an integer of from 1 to 4.

2. The compound according to claim 1, which is a compound selected from the group consisting SEQ ID NOS: 11, 12, 13, 14, 15, 16, 17, 18, 19, 20, 21, 22, 23, 24, 25, 26, 27 and 28.

3. The compound according to claim 1, in which n is 2 or 3.

4. The compound according to claim 1, in which F is one of the following side-chains

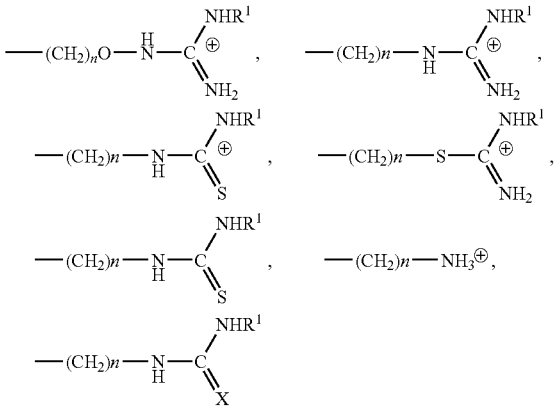

or another mimetic of an arginine side chain;

where

X is NCN, $NNO_2$, $CHNO_2$ or $NSO_2NH_2$;

n is an integer from 1 to 4, and $R^1$ is H or an alkyl, aryl, CN, $NH_2$, OH, —CO—$CH_2CH_3$, —CO—$CH_3$, —CO—$CH_2CH_2CH_3$, —CO—$CH_2Ph$, or —CO-Ph;

B is an indole, indole methyl, benzyl, phenyl, naphthyl, naphthyl methyl, cinnamyl group, or any other derivative of the aromatic group; and C is D- or L-cyclohexylalanine (Cha), leucine, valine, isoleucine, phenylalanine, tryptophan or methionine.

5. The compound according to claim 1, which has the formula

Ac-Phe-[Lys-Pro-(dCha)-Trp-Arg] or

Ac-Phe-[Orn-Pro-(dCha)-Trp-Arg].

6. The compound according to claim 1, in which A is L-arginine.

7. The compound according to claim 1, in which F is a L-amino acid.

8. The compound according to claim 7, in which F is L-arginine.

9. A composition comprising a compound according to claim 1, together with a pharmaceutically-acceptable carrier or excipient.

10. The composition according to claim 9, wherein in the compound of formula II, F is L-arginine.

11. The composition according to claim 9, wherein the compound of formula II is a compound selected from the group consisting SEQ ID NOS: 11, 12, 13, 14, 15, 16, 17, 18, 19, 20, 21, 22, 23, 24, 25, 26, 27 and 28.

12. The composition according to claim 9, wherein the compound of formula II has the formula Ac-Phe-[Lys-Pro-(dCha)-Trp-Arg] or Ac-Phe-[Orn-Pro-(dCha)-Trp-Arg].

13. The composition according to claim 9, in which F is L-arginine.

14. The composition of claim 9, wherein in the compound of formula II, F is a L-amino acid.

15. The compound according to claim 14, in which $R^1$ is methyl, ethyl, propyl, or butyl.

16. The composition according to claim 9, wherein in the compound of formula II F is one of the following side-chains

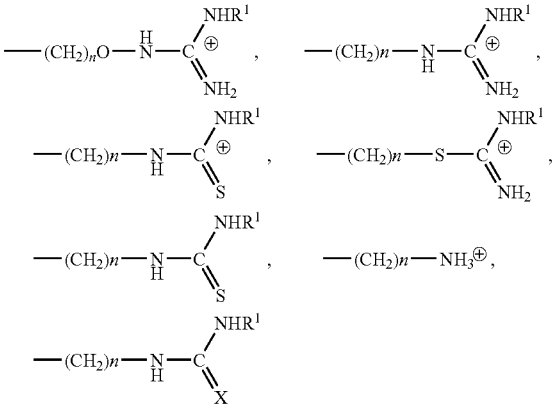

or another mimetic of an arginine side chain;

where

X is NCN, $NNO_2$, $CHNO_2$ or $NSO_2NH_2$;

n is an integer from 1 to 4, and $R^1$ is H or an alkyl, aryl, CN, $NH_2$, OH, —CO—$CH_2CH_3$, —CO—$CH_3$, —CO—$CH_2CH_2CH_3$, —CO—$CH_2Ph$, or —CO-Ph;

B is an indole, indole methyl, benzyl, phenyl, naphthyl, naphthyl methyl, cinnamyl group, or any other derivative of the aromatic group; and C is D- or L-cyclohexylalanine (Cha), leucine, valine, isoleucine, phenylalanine, tryptophan or methionine.

17. The composition according to claim 16, wherein in the compound of formula II, $R^1$ is methyl, ethyl, propyl, or butyl.

18. A method of antagonizing the activity of a C5a receptor on a cell, comprising contacting the cell with the compound of claim 1 in an amount sufficient to antagonize the activity of the C5a receptor on the cell.

19. The method according to claim 18, wherein in the compound of formula II, F is L-arginine.

20. The method according to claim 18, wherein the compound of formula II is a compound selected from the group consisting SEQ ID NOS: 11, 12, 13, 14, 15, 16, 17, 18, 19, 20, 21, 22, 23, 24, 25, 26, 27 and 28.

21. The method according to claim 18, wherein the compound of formula II has the formula Ac-Phe-[Lys-Pro-(dCha)-Trp-Arg] or Ac-Phe-[Orn-Pro-(dCha)-Trp-Arg].

22. The method according to claim 18, wherein in the compound of formula II, F is L-arginine.

23. The method of claim 18, wherein the cell is in a mammal and said contacting comprises administering the compound to said mammal.

24. The method according to claim 18, wherein in the compound of formula II, F is a L-amino acid.

25. The method of claim 24, wherein said mammal is a human.

26. The method according to claim 18, wherein in the compound of formula II F is one of the following side-chains

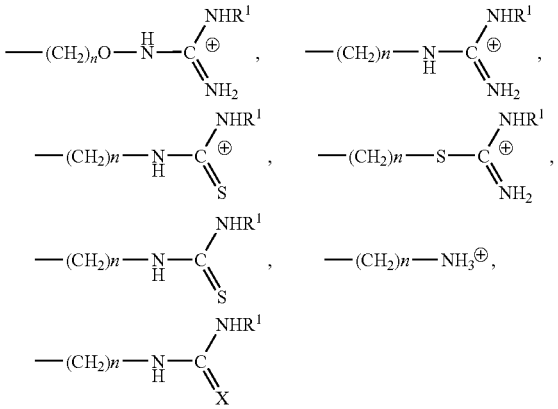

or another mimetic of an arginine side chain;

where

X is NCN, $NNO_2$, $CHNO_2$ or $NSO_2NH_2$;

n is an integer from 1 to 4, and $R^1$ is H or an alkyl, aryl, CN, $NH_2$, OH, —CO—$CH_2CH_3$, —CO—$CH_3$, —CO—$CH_2CH_2CH_3$, —CO—$CH_2Ph$, or —CO-Ph;

B is an indole, indole methyl, benzyl, phenyl, naphthyl, naphthyl methyl, cinnamyl group, or any other derivative of the aromatic group; and C is D- or L-cyclohexylalanine (Cha), leucine, valine, isoleucine, phenylalanine, tryptophan or methionine.

27. The method according to claim 26, wherein in the compound of formula II, $R^1$ is methyl, ethyl, propyl, or butyl.

28. A method of treating inflammatory arthritis mediated by a C5a receptor, comprising the step of administering an effective amount of a compound according to claim 10 to a mammal in need thereof.

29. The method of claim 28, wherein the mammal is a human.

30. The method of claim 28, wherein the inflammatory arthritis is rheumatoid arthritis.

31. A method of treating inflammatory arthritis, comprising the step of administering an effective amount of a compound according to claim 1 to a mammal in need thereof.

32. The method of claim 31, wherein the mammal is a human.

33. The method of claim 31, wherein the inflammatory arthritis is rheumatoid arthritis.

34. A compound which is an antagonist of the C5a receptor, and has the formula IV:

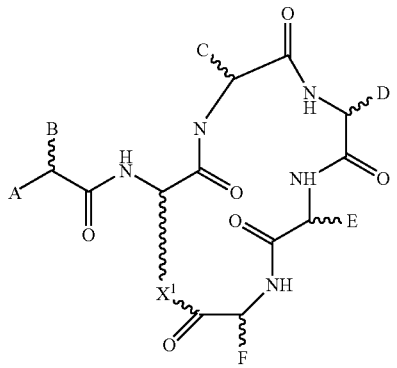

where A is any common or uncommon, basic, charged amino acid side chain which serves to position a positively charged group in this position;

B is a non-aromatic amino acid, and

C is any common or uncommon, hydrophobic amino acid side chain which serves to position any alkyl, aromatic or other group in this position; and D is any common or uncommon, aromatic amino acid which serve to position an aromatic side-chain in this position, and has the structure:

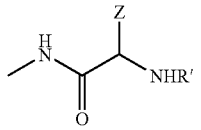

where Z is indole, indole methyl, benzyl, benzene, naphthyl, naphthyl methyl, or a derivative thereof; and R is H or an alkyl, aromatic, acyl or aromatic-acyl group;

E is any amino acid other than tryptophan and homotryptophan, and

F is the side chain of a D- or L-amino acid selected from the group consisting of arginine, homoarginine, lysine and homolysine.

35. A composition comprising a compound according to claim 34, together with a pharmaceutically acceptable carrier or excipient.

36. A method of agonizing the activity of a C5a receptor on a cell comprising contacting the cell with the compound of claim 34 in an amount sufficient to agonize the C5a receptor on the cell.

37. The method of claim 36, wherein the cell is in a mammal and said contacting comprises administering the compound to said mammal.

38. The method of claim 31, wherein the mammal is a human.

39. A method of treating inflammatory arthritis mediated by a C5a receptor, comprising the step of administering an effective amount of a compound according to claim 34 to a mammal in need thereof.

40. The method of claim 39, wherein the mammal is a human.

41. The method of claim 39, wherein the inflammatory arthritis is rheumatoid arthritis.

42. A method of treating inflammatory arthritis, comprising the step of administering an effective amount of a compound according to claim 34 to a mammal in need thereof.

43. The method of claim 42, wherein the mammal is a human.

44. The method of claim 42, wherein the inflammatory arthritis is rheumatoid arthritis.

45. A compound having the formula

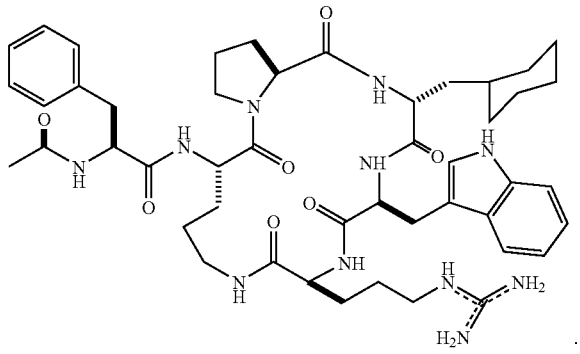

46. A composition comprising the compound of claim 45, together with a pharmaceutically acceptable carrier or excipient.

47. A method of agonizing the activity of a C5a receptor on a cell comprising contacting the cell with the compound of claim 45 in an amount sufficient to agonize the C5a receptor on the cell.

48. The method of claim 47, wherein the cell is in a mammal and said contacting comprises administering the compound to said mammal.

49. The method of claim 48, wherein the mammal is a human.

50. A method of treating inflammatory arthritis, comprising the step of administering an effective amount of a compound according to claim 45 to a mammal in need thereof.

51. The method of claim 50, wherein the mammal is a human.

52. A method of treating inflammatory arthritis mediated by a C5a receptor, comprising the step of administering an effective amount of a compound according to claim 45 to a mammal in need thereof.

53. The method of claim 52, wherein the mammal is a human.

54. The method of claim 52, wherein the inflammatory arthritis is rheumatoid arthritis.

* * * * *

UNITED STATES PATENT AND TRADEMARK OFFICE

CERTIFICATE OF CORRECTION

PATENT NO. : RE 41,287 E
APPLICATION NO. : 12/045088
DATED : April 27, 2010
INVENTOR(S) : Fairlie et al.

It is certified that error appears in the above-identified patent and that said Letters Patent is hereby corrected as shown below:

On the title page, Item (30), The Foreign Application Priority Data is incorrect. Item (30) should read:

-- (30) Foreign Application Priority Data

Jun. 25, 1997 (AU).....PO7559 --

Signed and Sealed this

Tenth Day of August, 2010

David J. Kappos

David J. Kappos
*Director of the United States Patent and Trademark Office*